US012755812B1

(12) United States Patent
Guruacharya et al.

(10) Patent No.: US 12,755,812 B1
(45) Date of Patent: Oct. 6, 2026

(54) OPTIMIZATION OF GENETIC SEQUENCES

(71) Applicant: Nanil Therapeutics Inc., Toronto (CA)

(72) Inventors: Anuj Guruacharya, Calgary (CA); Binita Rajbanshi, Toronto (CA)

(73) Assignee: Nanil Therapeutics Inc., Toronto (CA)

( * ) Notice: Subject to any disclaimer, the term of this patent is extended or adjusted under 35 U.S.C. 154(b) by 0 days.

(21) Appl. No.: 19/224,441

(22) Filed: May 30, 2025

Related U.S. Application Data

(60) Provisional application No. 63/784,214, filed on Apr. 6, 2025.

(51) Int. Cl.

| | |
|---|---|
| ***G01N 33/48*** | (2006.01) |
| ***G16B 5/20*** | (2019.01) |
| ***G16B 15/10*** | (2019.01) |
| ***G16B 30/20*** | (2019.01) |
| ***G16B 40/20*** | (2019.01) |

(52) U.S. Cl.
CPC ............... *G16B 30/20* (2019.02); *G16B 5/20* (2019.02); *G16B 15/10* (2019.02); *G16B 40/20* (2019.02)

(58) Field of Classification Search
None
See application file for complete search history.

(56) References Cited

U.S. PATENT DOCUMENTS

| | | | |
|---|---|---|---|
| 8,224,578 | B2 | 7/2012 | Raab |
| 10,941,409 | B2 | 3/2021 | Paul |
| 11,135,312 | B2 | 10/2021 | Von Der Mülbe |
| 11,183,271 | B2 | 11/2021 | Frey |
| 11,848,074 | B2 | 12/2023 | Lipowsky |
| 12,380,966 | B2 | 8/2025 | Essam |
| 2021/0366574 | A1 | 11/2021 | Fan |
| 2022/0348903 | A1 | 11/2022 | Ranganathan |
| 2023/0146324 | A1 | 5/2023 | Reynders, III |
| 2025/0210146 | A1 | 6/2025 | Repecka |

FOREIGN PATENT DOCUMENTS

EP 3660852 B1 5/2024

OTHER PUBLICATIONS

Lin, Brian C., et al. "In silico methods for predicting functional synonymous variants." Genome Biology 24.1 (2023): 126.*
Rajbanshi, B.; Guruacharya, A. CodonGPT: reinforcement learning on a generative language model enables scalable mRNA design. Nucleic Acids Research, 2025, vol. 53, No. 22, Oxford University Press, Oxford, UK.
Mauro, V.P.; Chappell, S.A. A critical analysis of codon optimization in human therapeutics. Trends in Molecular Medicine, 2014, pp. 604-613, vol. 20, Elsevier Ltd., Amsterdam, The Netherlands.
Consens, M.E.; Dufault, C.; Wainberg, M.; Forster, D.; Karimzadeh, M.; Goodarzi, H.; Theis, F.J.; Moses, A.; Wang, B. Transformers and genome language models, 2025, pp. 1-17, Nature Machine Intelligence, Springer Nature, London, UK.
Brandes, N.; Ofer, D.; Peleg, Y.; Rappoport, N.; Linial, M. ProteinBERT: a universal deep-learning model of protein sequence and function. Bioinformatics, 2022, pp. 2102-2110, vol. 38, Oxford University Press, Oxford, UK.
Ferruz, N.; Schmidt, S.; Höcker, B. ProtGPT2 is a deep unsupervised language model for protein design. Nature Communications, 2022, Article 4348, vol. 13, Springer Nature, London, UK.
Zhao, Y.; Oono, K.; Takizawa, H.; Kotera, M. GenerRNA: A generative pre-trained language model for de novo RNA design. PLoS One, 2024, Article e0310814, vol. 19, Public Library of Science, San Francisco, USA.
Yuan, Y.; Chen, Q.; Pan, X. DGRNA: a long-context RNA foundation model with bidirectional attention Mamba2. bioRxiv, 2024, Preprint 2024.10.31.621427, Cold Spring Harbor Laboratory, NY, USA.
Wang, N.; Bian, J.; Li, Y.; Li, X.; Mumtaz, S.; Kong, L.; Xiong, H. Multi-purpose RNA language modelling with motif-aware pretraining and type-guided fine-tuning. Nature Machine Intelligence, 2024, pp. 548-557, vol. 6, Springer Nature, London, UK.
Ji, Y.; Zhou, Z.; Liu, H.; Davuluri, R.V. DNABERT: pre-trained Bidirectional Encoder Representations from Transformers model for DNA-language in genome. Bioinformatics, 2021, pp. 2112-2120, vol. 37, OUP, Oxford, UK.
Ihtiyar, M.N.; Özgür, A. Generative language models on nucleotide sequences of human genes. Scientific Reports, 2024, Article 22204, vol. 14, Springer Nature, London, UK.
Gingold, H.; Pilpel, Y. Determinants of translation efficiency and accuracy. Molecular Systems Biology, 2011, Article 481, vol. 7, EMBO Press, Heidelberg, Germany.
Chung, B.K.-S.; Lee, D.-Y. Computational codon optimization of synthetic gene for protein expression. BMC Systems Biology, 2012, Article 134, vol. 6, BioMed Central, London, UK.
Mauro, V.P. Codon optimization in the production of recombinant biotherapeutics: potential risks and considerations. BioDrugs, 2018, pp. 69-81, vol. 32, Adis/Springer, Auckland, New Zealand.

(Continued)

*Primary Examiner* — Anna Skibinsky
(74) *Attorney, Agent, or Firm* — Goodwin Procter LLP

(57) ABSTRACT

The invention provides a system and method for generating biologically optimized codon sequences corresponding to a given protein sequence using a generative language model and reinforcement learning. A codon generation model receives an amino acid sequence and outputs a synonymous nucleotide sequence constrained by a codon masking mechanism to ensure translational fidelity. A composite reward function incorporating biologically relevant metrics, such as codon adaptation index (CAI), GC content, and mRNA folding stability, guides the optimization process. The model is fine-tuned using reinforcement learning to maximize the reward signal and produce codon sequences suitable for enhanced expression in specified host organisms. The system supports software-based deployment as an API or cloud interface and is applicable to synthetic biology, mRNA therapeutics, gene therapy, and protein manufacturing.

30 Claims, 9 Drawing Sheets

(56) References Cited

OTHER PUBLICATIONS

Burgess-Brown, N.A.; Sharma, S.; Sobott, F.; Loenarz, C.; Oppermann, U.; Gileadi, O. Codon optimization can improve expression of human genes in *Escherichia coli*: A multi-gene study. Protein Expression and Purification, 2008, pp. 94-102, vol. 59, Elsevier, Amsterdam, Netherlands.

Outeiral, C.; Deane, C.M. Codon language embeddings provide strong signals for use in protein engineering. Nature Machine Intelligence, 2024, pp. 170-179, vol. 6, Springer Nature, London, UK.

Grote, A.; Hiller, K.; Scheer, M.; Münch, R.; Nörtemann, B.; Hempel, D.C.; Jahn, D. JCat: a novel tool to adapt codon usage of a target gene to its potential expression host. Nucleic Acids Research, 2005, pp. W526-W531, vol. 33, OUP, Oxford, UK.

Puigbo, P.; Guzmán, E.; Romeu, A.; Garcia-Vallvé, S. Optimizer: a web server for optimizing the codon usage of DNA sequences. Nucleic Acids Research, 2007, Supplement 2, pp. W126-W131, vol. 35, Oxford University Press, Oxford, UK.

Hoover, D.M.; Lubkowski, J. DNAWorks: an automated method for designing oligonucleotides for PCR-based gene synthesis. Nucleic Acids Research, 2002, Article e43, vol. 30, OUP, Oxford, UK.

Raab, D.; Graf, M.; Notka, F.; Schodl, T.; Wagner, R. The GeneOptimizer Algorithm: using a sliding window approach to cope with the vast sequence space in multiparameter DNA sequence optimization. Systems and Synthetic Biology, 2010, pp. 215-225, vol. 4, Springer, New York, USA.

Villalobos, A.; Ness, J.E.; Gustafsson, C.; Minshull, J.; Govindarajan, S. Gene Designer: a synthetic biology tool for constructing artificial DNA segments. BMC Bioinformatics, 2006, Article 285, vol. 7, BioMed Central, London, UK.

Wolf, T.; Debut, L.; Sanh, V.; Chaumond, J.; Delangue, C.; Moi, A.; Cistac, P.; Rault, T.; Louf, R.; Funtowicz, M. HuggingFace's Transformers: State-of-the-art natural language processing. arXiv, 2019, Preprint arXiv:1910.03771.

Williams, R.J. Simple statistical gradient-following algorithms for connectionist reinforcement learning. Machine Learning, 1992, pp. 229-256, vol. 8, Springer, USA.

Fallahpour, A.; Gureghian, V.; Filion, G.J.; Lindner, A.B.; Pandi, A. CodonTransformer: a multispecies codon optimizer using context-aware neural networks. Nature Communications, 2025, Article 3205, vol. 16, Springer Nature, London, UK.

Jain, R.; Jain, A.; Mauro, E.; Leshane, K.; Densmore, D. ICOR: improving codon optimization with recurrent neural networks. BMC Bioinformatics, 2023, Article 132, vol. 24, BioMed Central, London, UK.

Goulet, D.R.; Yan, Y.; Agrawal, P.; Waight, A.B.; Mak, A.N.-S.; Zhu, Y. Codon optimization using a recurrent neural network. Journal of Computational Biology, 2023, pp. 70-81, vol. 30, Mary Ann Liebert Publishers, New Rochelle, NY, USA.

Giessel, A.; Dousis, A.; Ravichandran, K.; Smith, K.; Sur, S.; McFadyen, I.; Zheng, W.; Licht, S. Therapeutic enzyme engineering using a generative neural network. Scientific Reports, 2022, Article 1536, vol. 12, Springer Nature, London, UK.

Gupta, A.; Zou, J. Feedback GAN for DNA optimizes protein functions. Nature Machine Intelligence, 2019, pp. 105-111, vol. 1, Springer Nature, London, UK.

Yelmen, B.; Decelle, A.; Ongaro, L.; Marnetto, D.; Tallec, C.; Montinaro, F.; Furtlehner, C.; Pagani, L.; Jay, F. Creating artificial human genomes using generative neural networks. PLoS Genetics, 2021, Article e1009303, vol. 17, Public Library of Science, San Francisco, USA.

Li, S.; Moayedpour, S.; Li, R.; Bailey, M.; Riahi, S.; Kogler-Anele, L.; Miladi, M.; Miner, J.; Pertuy, F.; Zheng, D. CodonBERT large language model for mRNA vaccines. Genome Research, 2024, pp. 1027-1035, vol. 34, Cold Spring Harbor Laboratory Press, NY, USA.

Ren, Z.; Jiang, L.; Di, Y.; Zhang, D.; Gong, J.; Gong, J.; Jiang, Q.; Fu, Z.; Sun, P.; Zhou, B. CodonBERT: a BERT-based architecture tailored for codon optimization using the cross-attention mechanism. Bioinformatics, 2024, Article btae330, vol. 40, Oxford University Press, UK.

Eastman, P.; Shi, J.; Ramsundar, B.; Pande, V.S. Solving the RNA design problem with reinforcement learning. PLoS Computational Biology, 2018, Article e1006176, vol. 14, Public Library of Science, San Francisco, USA.

Stocco, F.; Artigues-Lleixa, M.; Hunklinger, A.; Widatalla, T.; Guell, M.; Ferruz, N. Guiding generative protein language models with reinforcement learning. arXiv, 2024, Preprint arXiv:2412.12979.

Subramanian, J.; Sujit, S.; Irtisam, N.; Sain, U.; Islam, R.; Nowrouzezahrai, D.; Kahou, S.E. Reinforcement Learning for Sequence Design Leveraging Protein Language Models. arXiv, 2024, Preprint arXiv:2407.03154.

Rajbanshi, B.; Guruacharya, A. codonGPT: Reinforcement learning on a generative language model optimizes RNA sequences under biological constraints. bioRxiv, 2025, Preprint bioRxiv: Jun. 2025.

Lin, B.C.; Katneni, U.; Jankowska, K.I.; Meyer, D.; Kimchi-Sarfaty, C. In silico methods for predicting functional synonymous variants. Genome Biology, 2023, Issue 1, Article 126, vol. 24, Springer Nature, London, UK.

* cited by examiner

OPTIMIZATION OF GENETIC SEQUENCES

CROSS-REFERENCE TO RELATED APPLICATIONS

This application claims the benefit of U.S. Provisional Patent Application No. 63/784,214, filed on Apr. 6, 2025, entitled "A system and method for generating codon-optimized nucleotide sequences using generative transformer-based models and biological constraints," which is incorporated herein by reference in its entirety.

PRIOR ART

Conventional mRNA sequence optimization methods primarily rely on deterministic algorithms or frequency-based substitution strategies, which replace each amino acid with the most used synonymous codon in a target organism. These methods lack the ability to simultaneously optimize for multiple biological constraints such as codon adaptation index (CAI), GC content, RNA folding stability, or repeat suppression, and often produce biologically suboptimal sequences with limited diversity. More recent approaches have incorporated deep learning models to generate or score codon sequences, but these are typically trained in a supervised fashion and do not incorporate reinforcement learning to iteratively improve sequences based on biologically grounded reward functions. Furthermore, existing models generally do not account for trade-offs across multiple molecular properties during codon selection, nor do they preserve synonymous diversity in a controlled or tunable manner. Accordingly, there remains a need for a codon generation system that integrates reinforcement learning with multi-objective biological constraints to produce optimized, diverse, and biologically viable mRNA sequences.

BACKGROUND OF THE INVENTION

In synthetic biology and protein engineering, optimizing codon sequences to maximize protein expression in a specific host organism is essential. Traditional codon optimization methods rely on codon usage frequency tables and fail to account for complex biological constraints or context-dependent effects. Furthermore, existing approaches do not leverage recent advances in deep learning and generative models, which have proven powerful in natural language and sequence generation tasks. A need exists for a system that can learn codon usage patterns from biological data, enforce amino acid fidelity through synonymous constraints, and optimize sequences using biologically informed reward functions.

SUMMARY OF THE INVENTION

The invention discloses systems and methods for generating codon sequences corresponding to a protein sequence using a generative language model fine-tuned via reinforcement learning. While the model is initially pretrained to learn codon usage patterns, the core novelty lies in applying biologically informed constraints and reward optimization during a reinforcement learning phase. At each decoding step, codon outputs are restricted to valid synonymous options. The model is then fine-tuned using a reward function that captures organism-specific biological metrics, including codon adaptation index (CAI), GC content, mRNA secondary structure stability (deltaG), codon repetition penalties, and positional entropy. Reinforcement learning with these custom reward signals leads to codon sequences that improve biological characteristics without altering the encoded protein. This reward-driven generation approach, guided by biological priors and structural constraints, significantly outperforms static codon frequency methods and naive language models in optimizing for real-world expression efficiency, stability, and genetic fidelity. The invention has applications in mRNA therapeutics, synthetic biology, gene therapy, and biotechnology.

DETAILED DESCRIPTION OF THE INVENTION

Overview of the Invention

The present invention relates to systems and methods for codon sequence optimization in nucleic acid engineering, more specifically, to a reinforcement learning-based system that generates biologically favorable codon sequences encoding a target polypeptide. The invention enables simultaneous optimization of multiple biological constraints, including but not limited to codon adaptation index (CAI), guanine-cytosine (GC) content, RNA secondary structure stability (deltaG), codon repeat minimization, and output sequence diversity.

Traditional codon optimization approaches rely on frequency-based or constraint-satisfaction heuristics, such as choosing the most used codons in the host organism (e.g., based on CAI) or eliminating rare codons. These approaches typically optimize one objective and often fail to account for complex biological trade-offs, such as over-stabilizing mRNA structures, introducing harmful motifs, or reducing sequence diversity across constructs. Existing commercial tools (e.g., DNA Chisel, GenSmart, ICOR) generally use static, rule-based algorithms that cannot adapt to nuanced downstream objectives.

In contrast, the present invention introduces a data-driven framework that trains a generative model to sample codon sequences conditioned on an amino acid input while learning from a biologically motivated, multi-objective reward function. This is achieved through reinforcement learning (RL), where the model is rewarded for generating codon sequences that encode the correct protein while simultaneously satisfying a set of desired biological constraints.

At a high level, the system accepts a fixed amino acid sequence as input and uses a generative model—such as a transformer decoder—to produce codon sequences. Each candidate codon sequence is evaluated using a composite reward function that includes shaped versions of CAI, GC content, and deltaG, along with penalty terms for codon repetition and optional diversity scores. The reward is then used to update the model using reinforcement learning algorithms, such as REINFORCE or other policy gradient techniques.

Figure 1:
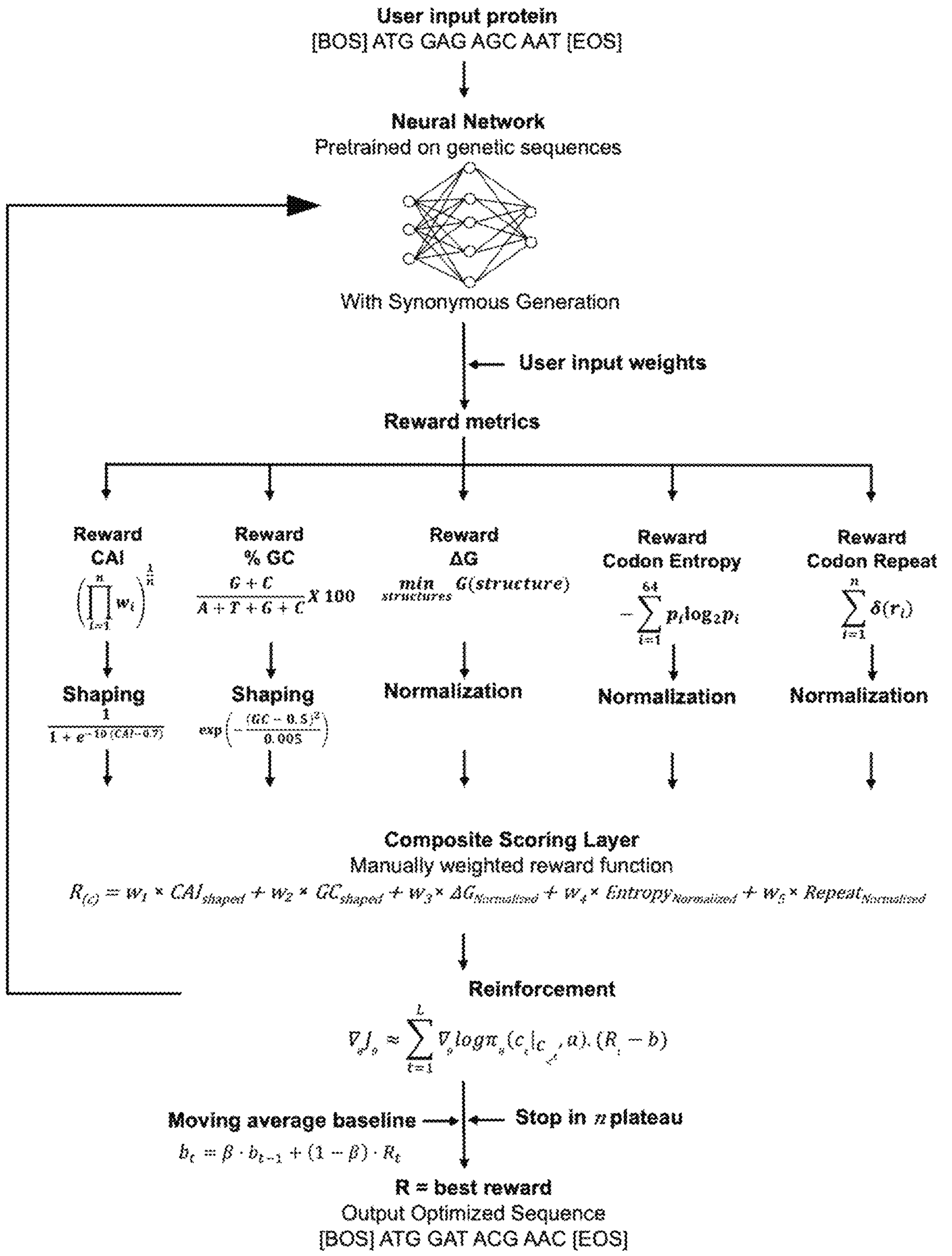
FIG. 1 is an overview of the method flowchart.

A representative system flow is illustrated in FIG. 1, which shows the full loop of codon generation, reward computation, and model updating. The system may also include optional pretraining steps on codon-protein pairs, post-generation filtering, and downstream integration with synthesis pipelines or bioinformatics tools.

This invention is intended for use in a wide variety of biotechnological applications, including mRNA vaccine design, protein expression optimization, synthetic biology circuit design, and DNA construct synthesis. Because the model is adaptable and supports customizable reward terms, it offers a generalizable and future-proof platform for codon sequence optimization.

The novelty of the invention lies in its use of (i) reinforcement learning for biological sequence generation, (ii) biologically shaped reward functions across multiple simultaneous objectives, (iii) codon-restriction-aware sampling using synonym masking, and (iv) explicit diversity controls to avoid mode collapse or degenerate optimization.

DEFINITIONS AND TERMINOLOGY

For the purposes of the present disclosure, the following terms and abbreviations shall have the meanings set forth below. These definitions are intended to aid clarity and consistency and are not intended to limit the scope of the invention, which is defined solely by the claims.

Codon sequence: A linear sequence of nucleotide triplets (codons), each of which encodes a corresponding amino acid residue or a translation stop signal.

Synonymous codon: A codon that encodes the same amino acid as another codon. For example, both GAA and GAG encode glutamic acid. Synonymous codons are interchangeable at the protein level but may differ in translational efficiency or regulatory effect.

Codon adaptation index (CAI): A numerical score reflecting the relative usage frequency of each codon in a given host organism. Higher CAI values typically correlate with improved translation efficiency. CAI values are normalized between 0 and 1.

GC content: The fraction of guanine (G) and cytosine (C) nucleotides in a sequence. GC content affects mRNA stability, secondary structure, and synthesis efficiency.

RNA folding energy (deltaG): A thermodynamic value, typically in kcal/mol, representing the predicted free energy of RNA secondary structure formation. More negative deltaG values generally indicate more stable RNA structures.

Codon repeat penalty: A reward term or penalty score applied to discourage consecutive repeated codons (e.g., AAA AAA AAA). Repeated codons may result in ribosomal stalling or synthesis errors.

Entropy: A measure of diversity in the codon sequence, typically computed using

Shannon entropy across positions or across sequences. Higher entropy indicates broader usage of the codon space and reduced risk of mode collapse.

Levenshtein distance: A metric that quantifies the number of edits (insertions, deletions, or substitutions) required to transform one codon sequence into another. Used as a diversity measure between candidate sequences.

Codon generation model: A probabilistic language model that outputs codon sequences conditioned on input amino acid sequences. The model may be transformer-based, LSTM-based, or another neural architecture.

Logit masking: A method used during inference to constrain the model's output to valid codons for a given amino acid. The model's output logits are modified such that non-synonymous codons are suppressed or zeroed.

Reinforcement learning (RL): A machine learning paradigm in which the model learns to make decisions by maximizing a reward signal. In this invention, RL is used to optimize codon sequence generation by maximizing biologically motivated rewards.

Policy gradient method: A reinforcement learning algorithm that adjusts model parameters in the direction of the reward gradient. The REINFORCE algorithm is a common example, and is used in one embodiment of this invention.

Computer-readable medium (CRM): Any non-transitory storage medium containing computer-executable instructions that, when executed, cause a computing system to perform any of the methods described herein.

Host organism: The intended expression system for the codon-optimized gene (e.g., *Escherichia coli, Saccharomyces cerevisiae*, CHO cells, or human cells), which may influence reward parameters such as CAI tables or GC targets.

Target expression context: The biological or clinical context in which the codon-optimized sequence will be deployed, including recombinant expression, therapeutic application, or synthetic biology usage.

Input and Output Specification

In various embodiments, the system receives a fixed amino acid sequence as input and generates one or more optimized synonymous codon sequences as output. Each output sequence encodes the identical polypeptide as the input, but is optimized according to multiple biological constraints as described herein. This section defines the input and output specification formats, including optional metadata that may guide model behavior.

The input to the system consists of a linear amino acid sequence, represented in one of several acceptable formats. These formats may include, but are not limited to, a plain-text string of single-letter amino acid codes, a FASTA-formatted file, or a structured JSON object containing sequence and metadata. The amino acid sequence may correspond to full-length proteins, open reading frames (ORFs), fusion constructs, epitopes, or engineered sequence variants.

In all cases, the input protein sequence is treated as immutable. The codon generation module is configured to maintain synonymous fidelity, ensuring that the output nucleotide sequence translates to the exact same polypeptide using the standard genetic code or a user-defined codon table. The model does not modify, truncate, or extend the input protein sequence.

In some embodiments, the input may be accompanied by contextual metadata. Such metadata may include: a target host organism (e.g., *Escherichia coli*, CHO cells, HEK293), desired GC content bounds or preference profiles, a reference organism identifier for codon adaptation index (CAI) computation, the intended expression modality (e.g., in vitro transcription, mRNA therapeutics, recombinant protein production), or identifiers such as project tags, timestamps, or sequence IDs.

These optional metadata fields may be used to dynamically influence reward function weighting, codon masking tables, filtering strategies, or downstream export formatting. This allows the system to be flexibly adapted to multiple biological contexts without retraining or architectural modification.

The output of the system consists of one or more codon sequences that are synonymous to the input amino acid sequence. Each output sequence is a linear nucleotide string composed of non-overlapping triplet codons. The output codons are constrained by the standard or user-specified genetic code and preserve the original translation.

Output sequences may be returned in one or more machine-readable formats, including but not limited to: plain-text DNA strings, CSV files with one sequence per row, FASTA-formatted records, JSON objects containing reward scores and metadata, or GenBank-formatted annotations for integration with downstream software tools such as cloning, synthesis, or regulatory submission pipelines.

In some embodiments, each output sequence is accompanied by a reward vector, which includes the individual component scores used during optimization. This may include, for example: the codon adaptation index (CAI), GC percentage, RNA folding energy (deltaG), repeat penalty or repeat count, codon sequence diversity score (e.g., entropy or average Levenshtein distance), and a final scalar reward score. These values provide interpretability and traceability of the optimization process.

Output sequences may be filtered or ranked according to total reward score, diversity relative to other sequences, similarity to native codon usage, or other user-specified criteria. In some embodiments, the user may specify constraints on output count or quality, such as generating the top N sequences by reward score, or including only sequences above a defined threshold. Sequence generation strategies may include stochastic sampling, beam search, or diversity-controlled sampling mechanisms.

In one embodiment, the system supports batch input and parallelized generation, enabling high-throughput production of codon-optimized libraries for multiple proteins or for variant libraries derived from a single input sequence. This capability supports use cases such as combinatorial screening, synthetic gene assembly, and data-driven codon sequence exploration.

Codon Generation Model Architecture

In various embodiments, the codon generation system comprises a probabilistic, autoregressive sequence model configured to output codon-level nucleotide sequences conditioned on a fixed amino acid sequence. The model architecture may include, but is not limited to, a transformer decoder, a long short-term memory (LSTM) network, or any neural network capable of modeling sequential dependencies and context-aware token generation.

In a representative embodiment, the system utilizes a transformer decoder architecture. The transformer comprises one or more decoder layers that receive tokenized amino acid embeddings, optionally combined with positional encodings. At each decoding step, the model outputs a probability distribution over the 64 canonical codons, which is subsequently filtered using synonym masking, as described below.

The model generates sequences one codon at a time, where each prediction is conditioned on the full context of the input amino acid sequence and the previously generated codons. The decoder is explicitly constrained not to emit stop codons unless the input amino acid sequence ends with a termination symbol. Model parameters may be initialized either randomly or through pretraining on codon-protein sequence pairs.

The model may be implemented using deep learning frameworks such as PyTorch, TensorFlow, or JAX. Training may be performed using minibatch or online learning procedures. The architectural parameters—such as embedding size, number of layers, attention heads, dropout rate, and context window size—may be configurable and are not intended to limit the scope of the invention.

In some embodiments, the system employs a shared embedding space for amino acid and codon representations, enabling joint learning across input and output domains. Tokenization is performed at the codon level, using fixed triplet representations. Sequences may be padded or truncated to uniform length during training to accommodate batch-wise optimization.

During inference, codon sequences are generated using one or more sampling strategies, including but not limited to Greedy decoding, Top-k sampling, Nucleus (top-p) sampling, and Beam search. In some configurations, diversity penalties or entropy-based regularization may be applied to encourage exploration of the synonymous codon space.

To ensure biological correctness, the model incorporates a synonym-constrained inference mechanism. For each input amino acid position, the model's output distribution is masked such that only synonymous codons, under the defined genetic code, are permitted. This synonym mask is applied at the logit level prior to sampling or decoding.

In certain embodiments, the codon synonym mask is precomputed and stored as a lookup table indexed by amino acid. In other embodiments, the mask is dynamically constructed at runtime using either the standard genetic code or a user-defined codon table, allowing flexibility for non-standard organisms or synthetic translation systems.

This synonym constraint ensures that all generated nucleotide sequences remain translationally equivalent to the input amino acid sequence, reducing the risk of biologically invalid output. Additionally, it improves training efficiency by limiting the effective output space to biologically plausible options and focusing the optimization on synonymous variation rather than error correction.

In more advanced configurations, the output logits may be further adjusted using temperature scaling, reward-based biasing, or history-aware regularization. For example, codons observed more frequently during training may be assigned higher weights, or specific codons may be favored based on reward feedback to steer the model toward desired biological properties.

Pretraining Phase

In some embodiments, the codon generation model is initialized through a pretraining phase conducted prior to reinforcement learning. The primary objective of pretraining is to expose the model to biologically valid codon-amino acid pairings derived from naturally occurring sequences. This initialization improves the model's familiarity with codon usage conventions, reduces the frequency of biologically implausible outputs, and enhances the stability and convergence rate of downstream reinforcement learning updates.

Pretraining is performed using supervised learning, where the training dataset comprises paired codon and amino acid sequences. These examples may be sourced from publicly available biological databases such as RefSeq, Ensembl, or UniProt, which contain extensive collections of gene and protein sequences derived from diverse host organisms.

Each training example consists of amino acid sequence A={a1, a2, a3, . . . , aN} or codon sequence C={c1, c2, c3, . . . , cN} such that Translate (C)=A. The model is trained to generate the correct codon at each position, conditioned on the amino acid and preceding codons, by minimizing the cross-entropy loss between the predicted and reference codons.

The training objective during pretraining is to maximize the log-likelihood of the ground-truth codon sequence, given the fixed amino acid context. In some embodiments, synonym masking is applied during supervised training to ensure that predicted codons are selected only from the set of valid synonyms for each amino acid. This constraint helps the model focus on codon preference learning rather than translation fidelity enforcement.

Through this training process, the model learns several biologically relevant properties. These include (i) amino acid-codon association frequencies (e.g., common synonymous mappings), (ii) context-dependent codon pair preferences (e.g., codon-codon adjacency biases), and (iii) host-specific codon usage biases, particularly if the training data are stratified by organism.

In some implementations, the supervised learning task is augmented with additional biological annotations to enhance codon preference learning. These may include codon adaptation index (CAI) scores, GC content labels, ribosome profiling-derived codon usage frequencies, or position-specific scoring matrices (PSSMs) indicating synonymous codon probabilities at each position.

The output of the pretraining phase is a set of model weights that serve as the initialization point for reinforcement learning. This allows the policy network to begin from a codon usage space that is biologically plausible and avoids the need for extensive exploration from random initialization. Empirically, this strategy reduces the frequency of invalid codon outputs during early training epochs and improves convergence speed and final sequence quality.

In some configurations, pretraining may be skipped, and the model may be trained from scratch using reinforcement learning alone. However, pretraining typically yields superior performance in terms of learning stability, codon quality, and convergence time, especially for longer protein sequences or expression systems with strong codon preferences.

The pretrained model checkpoint may be serialized and stored in standard formats such as .pt, .ckpt, or .h5. These files may be version-controlled and registered in software repositories or model registries to support reproducibility, auditability, and reuse across different codon optimization runs or biological applications.

Reinforcement Learning Procedure

In various embodiments of the present invention, the codon sequence generation model is fine-tuned using a reinforcement learning (RL) algorithm, where the training objective is to maximize the expected reward over the distribution of generated synonymous codon sequences. The model learns to generate codon sequences that are biologically optimized, as measured by the composite reward function.

In one embodiment, the RL algorithm used is the REINFORCE policy gradient method, which is particularly suitable for stochastic sequence generation tasks involving scalar reward signals. At each training step, the model samples a codon sequence from its current policy, evaluates it using the reward function, and updates the model parameters to increase the expected reward via gradient ascent.

The policy gradient update is computed according to the REINFORCE rule, as expressed in Equation 1.

$$\text{gradient} = (\text{reward} - \text{baseline}) \times \text{gradient of log probability of the codon sequence} \quad \text{[Equation 1]}$$

In Equation 1, "reward" represents the total scalar biological reward assigned to the sampled codon sequence, "baseline" refers to a moving average of previous reward values used for variance reduction, and the "gradient of log probability" is computed with respect to the model's parameters.

The log probability of a codon sequence is computed as the sum of the log probabilities at each codon position, as shown in Equation 2.

$$\text{log\_prob} = \log(p1) + \log(p2) + \ldots + \log(pL) \quad \text{[Equation 2]}$$

In Equation 2, L denotes the number of codon positions in the input protein sequence, and p1, p2, p3, etc. is the model's probability of selecting the codon at position 1, 2, 3, etc., conditioned on the corresponding amino acid and context.

This learning algorithm incentivizes the model to assign higher probabilities to codon sequences that achieve higher biological reward scores, thereby increasing the expected biological fitness of its outputs. The training loop enables unsupervised optimization using only reward feedback, without requiring explicit codon label supervision.

A typical reinforcement learning cycle comprises the following steps: (a) sampling protein sequences from a training dataset, (b) generating synonymous codon sequences using synonym-constrained sampling, (c) computing the composite reward for each codon sequence, (d) calculating the policy gradient using the difference between reward and baseline, (e) updating model parameters using a gradient-based optimizer (e.g., Adam), and (f) updating the baseline using an exponential moving average of previous rewards.

To ensure training stability, the system may implement one or more of the following techniques: (a) reward normalization, in which a moving baseline is subtracted from the raw reward to stabilize gradients; (b) entropy regularization, in which a term is added to the loss function to encourage exploration and prevent early determinism; and (c) gradient clipping, which limits the magnitude of parameter updates to avoid instability during optimization.

In some embodiments, curriculum learning is used to gradually increase reward complexity. For example, the model may initially be trained using only a subset of reward terms (e.g., CAI and GC content), with additional terms (e.g., deltaG, codon diversity) introduced in later training stages to prevent reward imbalance and premature convergence.

Figure 2:
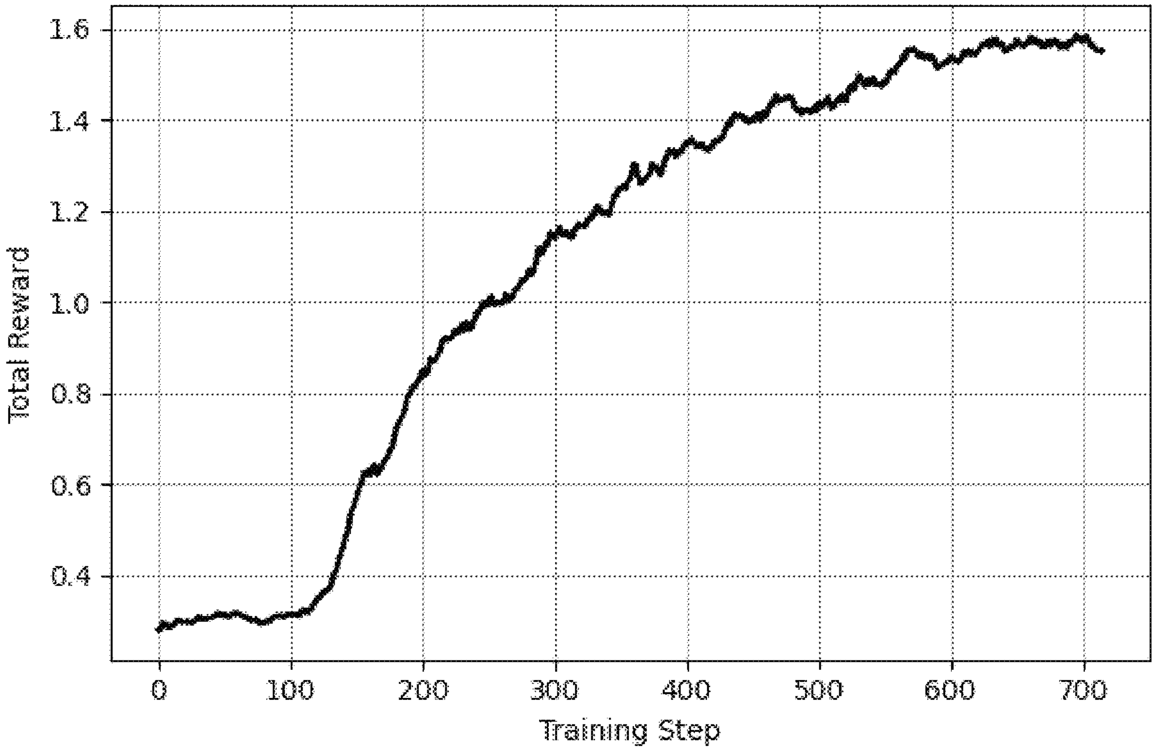
FIG. 2 is a line plot showing the increase of the reward metric as the training steps for the reinforcement learning increases.

Training progress may be monitored by plotting scalar reward values over time. FIG. 2 shows an example of training progression and change in reward values for optimization of the ACTB gene.

The reinforcement learning procedure continues until convergence criteria are met. These criteria may include a plateau in validation reward, the attainment of a predefined performance threshold, or the completion of a fixed number of iterations. Upon convergence, the final model checkpoint constitutes a biologically optimized codon generator that produces sequences which are both synonymous with the input protein and tailored to maximize defined biological objectives.

Reward Function Components for Reinforcement Learning

In various embodiments of the present invention, a biologically informed reward function is utilized to evaluate codon sequences generated by the model. This reward function provides scalar feedback to guide reinforcement learning toward sequences that are not only synonymous with the input protein sequence but also optimized for one or more biologically significant properties. The objective is to reward sequences that maintain the original amino acid sequence while exhibiting improved performance in terms of translational efficiency, molecular stability, and other expression-related factors.

Figure 3:
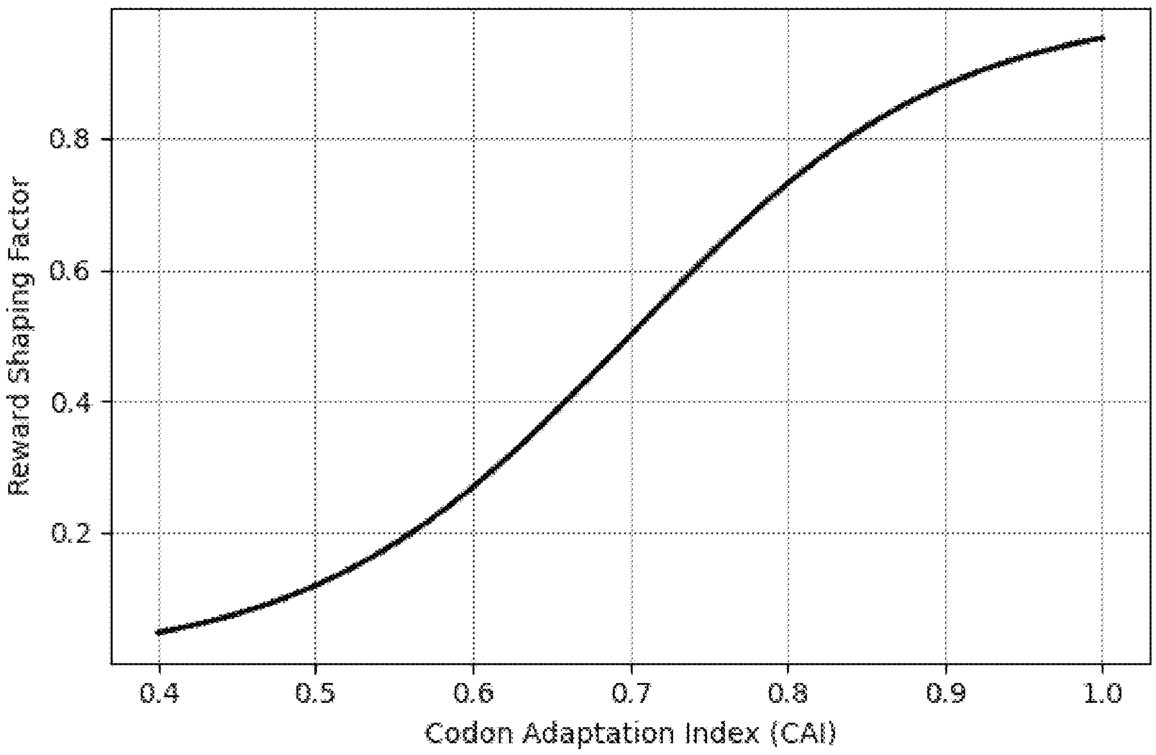
FIG. 3 is a line plot showing the shaping of reward components, CAI.
Figure 4:
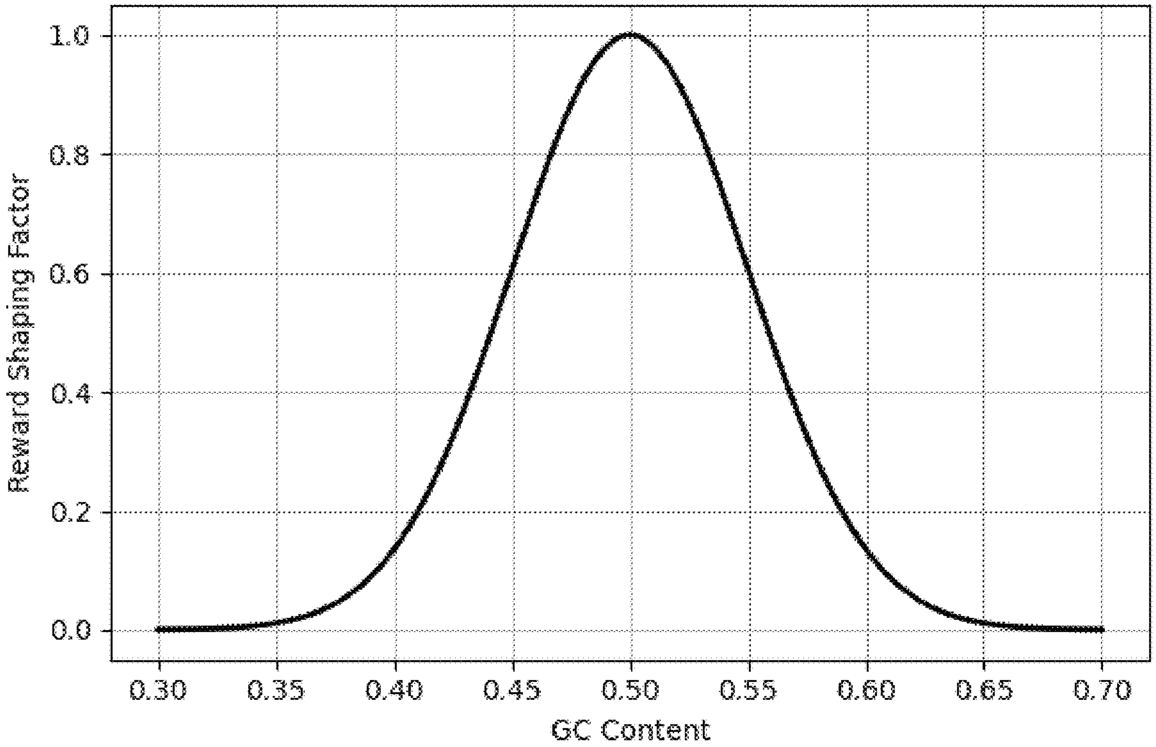
FIG. 4 is a line plot showing the shaping of reward components, GC.

The reward function is constructed as a weighted combination of multiple biologically relevant metrics. These metrics may include, but are not limited to, codon adaptation index (CAI), GC content stability, RNA folding energy (deltaG), codon repeat suppression, and codon usage entropy. Each metric may be individually normalized to a scale between 0 and 1, and optionally shaped using mathematical transformations such as sigmoid or piecewise-linear functions to improve the gradient properties of the reward signal. This normalization and shaping process allows for more effective training by avoiding vanishing gradients and reducing the risk of over-optimization for any single metric. FIG. 3 and FIG. 4 show examples of shaping for the CAI reward component and the GC reward component, respectively.

The final scalar reward used in reinforcement learning is computed as a weighted combination of the normalized and shaped component scores. An example formulation of the total reward is provided in Equation 3.

$$\text{total\_reward} = w1 * \text{CAI\_score} + w2 * \text{GC\_penalty} + w3 * \text{deltaG\_score} + w4 * \text{repeat\_score} + w5 * \text{entropy} \quad \text{[Equation 3]}$$

In this formulation, CAI_score, GC_penalty, deltaG_score, repeat_score, and entropy represent the metrics for a given codon sequence, and w1 through w5 are their respective scalar weights. These weights may be set manually by the user, inferred from application requirements, or dynamically adjusted by the system during training.

In some embodiments, the composition of the reward vector may be modified to suit specific applications. Certain metrics may be excluded, new metrics may be included, or the weight values may be adapted in real time to reflect optimization goals such as therapeutic mRNA stability, immunogenicity minimization, or codon orthogonality in synthetic gene circuits. The reward function is thus modular and configurable, allowing it to generalize across multiple use cases within codon optimization for protein expression in diverse biological systems.

CAI as Reward Component

In some embodiments, the invention incorporates Codon Adaptation Index (CAI) as a biologically motivated metric to guide codon optimization. CAI is a widely accepted quantitative measure that evaluates how closely a codon sequence adheres to the codon usage bias of a specified host organism. This metric serves as a proxy for the expected translational efficiency and expression level of the corresponding protein. Organism-specific codon usage tables—derived from experimentally validated datasets or user-defined profiles—are used to compute CAI values. These tables may be selected manually by the user or automatically inferred by the system based on the intended expression host.

In various embodiments, the CAI metric may be incorporated into the reward function either as a raw CAI score or as a transformed score that enhances learning stability and biological interpretability. In certain implementations, the raw CAI value is passed through a sigmoid shaping function to produce a smooth, non-linear transformation that mitigates reward saturation and sharp gradients near high CAI values.

This transformation provides a biologically interpretable and tunable incentive structure that encourages codon sequences with CAI values above a defined target threshold, rather than indiscriminately collapsing to the most frequent codons. The normalized CAI reward, referred to herein as CAI_score, may be computed as in Equation 4.

$$\text{CAI\_score} = 1/(1 + \exp(-k * \text{CAI\_raw} - \text{CAI\_target}))) \quad \text{[Equation 4]}$$

In Equation 4, "CAI_raw" is the unnormalized codon adaptation index, "CAI_target" is a configurable parameter representing the target efficiency threshold (e.g., 0.85), and "k" is a user-defined steepness parameter controlling the gradient sensitivity of the reward function. An example visualization of the CAI shaping function as a transformation is illustrated in FIG. 3.

The use of a shaped reward enables gradient-aware reinforcement learning that promotes biologically realistic codon distributions while preserving synonymous variability. In some embodiments, the system may dynamically adjust the CAI_target or k value during training to enforce adaptive optimization objectives.

GC Content as Reward Component

In various embodiments of the present invention, GC content is incorporated into the reward function to influence the nucleotide composition of the generated codon sequence. GC content is a biologically meaningful feature that impacts several downstream properties, including mRNA stability, synthetic cost, and unintended interactions with regulatory elements such as CpG islands or RNA-binding motifs. To encourage biologically favorable expression and manufacturing characteristics, the model is configured to generate sequences whose GC content approaches a user-specified or system-determined target GC percentage, such as 50%.

In some embodiments, a penalty is applied to sequences whose GC content deviates from the desired target value. This penalty may be implemented using a Gaussian shaping function, a triangular penalty function, or stepwise cut-off thresholds, depending on the precision required by the application. The Gaussian variant provides a smooth, differentiable curve that penalizes both over- and under-representation of GC nucleotides, while preserving gradient signal for reinforcement learning.

An example of a GC reward function using a Gaussian penalty centered on the target GC value is given in Equation 5.

$$GC\_penalty = \exp(-((GC\_actual - GC\_target)^{\wedge}2)/(2*sigma^{\wedge}2)) \quad \text{[Equation 5]}$$

In Equation 5, GC_actual represents the actual GC content of the codon sequence (expressed as a percentage), GC_target is the preferred value (e.g., 50%), and sigma is a tunable parameter that controls the width of the penalty curve (e.g., sigma=10). This formulation yields a scalar value between 0 and 1, where values closer to 1 indicate closer alignment with the GC target. A visualization of this function is shown in FIG. 4.

In certain embodiments, GC content may be computed over the entire codon sequence to yield a global penalty score. Alternatively, in more advanced configurations, GC content may be assessed within sliding windows of predefined lengths (e.g., 30 nucleotides), thereby enabling localized control over sequence composition and minimizing regions of high GC clustering or low GC depletion. This localized GC control may be beneficial in optimizing for mRNA folding, ribosome processivity, or sub-regional secondary structure.

RNA Folding Energy as a Reward Component

In various embodiments of the present invention, RNA secondary structure stability, as quantified by minimum free energy (deltaG), is used as a reward function component to guide the generation of codon sequences that optimize post-transcriptional performance. RNA folding energy plays a critical role in determining mRNA degradation rate, translation efficiency, and innate immune activation. While moderately stable structures may confer protection and translational benefits, excessively stable configurations—such as long hairpin loops or pseudoknots—may hinder ribosomal access and translation initiation. Therefore, the reward function is shaped to balance stability and accessibility by penalizing sequences that fall outside a biologically optimal deltaG range.

In some embodiments, the deltaG value is computed using computational RNA secondary structure prediction tools, including but not limited to ViennaRNA (RNAfold), and normalized on a per-nucleotide basis to account for sequence length. The reward score associated with RNA folding energy may be computed using a linear normalization formula as shown in Equation 6.

$$deltaG\_score = 1 - ((deltaG\_per\_nt - min\_dG)/(max\_dG - min\_dG)) \quad \text{[Equation 6]}$$

In Equation 6, deltaG_per_nt refers to the predicted free energy of folding per nucleotide (expressed in kcal/mol/nt). The variables min_dG and max_dG define the biologically acceptable lower and upper bounds for RNA folding stability (e.g., min_dG=−0.6, max_dG=0.0). The resulting deltaG_score is a normalized value between 0 and 1, where higher values indicate a more favorable range of folding energy.

In certain embodiments, the normalized deltaG value may be further transformed or shaped using non-linear functions (e.g., Gaussian, sigmoid) to modulate sensitivity near the stability thresholds. Additionally, the folding energy may be evaluated globally across the full mRNA sequence, or locally within defined regions such as the 5' UTR or coding sequence (CDS), depending on the application requirements. This modular configuration allows the system to penalize overly stable structures in critical regulatory regions while tolerating moderate stability elsewhere.

Codon Repeat Penalty as a Reward Component

In various embodiments of the present invention, a codon repeat penalty is incorporated into the reward function to discourage the generation of codon sequences that contain repetitive trinucleotide motifs. Repeated codon triplets, particularly consecutive identical codons, are known to cause ribosomal stalling, co-translational misfolding, and reduced protein synthesis efficiency. By penalizing adjacent codon repeats, the model is encouraged to generate synonymous codon sequences with greater translational robustness and biological reliability.

The codon repeat penalty is computed by identifying consecutive identical codons within the generated sequence and quantifying their frequency. A normalized score is then calculated using Equation 7.

$$repeat\_score = 1 - (repeat\_count/(total\_codons - 1)) \quad \text{[Equation 7]}$$

In Equation 7, repeat_count denotes the number of adjacent repeated codons in the generated sequence, and total_codons refers to the total number of codons in the sequence. The subtraction of one from total_codons accounts for the number of adjacent pairs that can be formed within the sequence.

The resulting repeat_score is a scalar value bounded between 0 and 1, where a value of 1 indicates no codon repetition and a value approaching 0 indicates high redundancy. This scoring mechanism ensures that sequences with frequent adjacent repeats are penalized during training, thereby reducing the likelihood of translational pausing and improving overall protein synthesis fidelity. In some embodiments, the system may further refine the penalty by considering repeat length thresholds, repeat density, or repetition of rare codons specifically.

Diversity as a Reward Component

In various embodiments of the present invention, a diversity-based reward component is included in the codon optimization framework to promote sequence variability and prevent mode collapse during model training. This component encourages the generation of distinct but synonymous codon sequences for a fixed protein input, thereby expanding the effective design space, enhancing biological robustness, and increasing flexibility in downstream applications such as synthetic biology, immunogenicity modulation, and regulatory compliance.

In one embodiment, codon diversity is quantified using positional entropy, calculated from the empirical distribution of codon usage across a batch of generated sequences. Let p_i,j denote the frequency with which codon i appears at codon position j across the batch. The entropy at position j is computed using the Shannon entropy formula, as shown in Equation 8.

$$H\_j = -(p\_1, j*\log2(p\_1, j) + p\_2, j)*\log2(p\_2, j) + \ldots + p\_k, j*\log2(p\_k, j)) \quad \text{[Equation 8]}$$

In Equation 8, H_j represents the entropy at codon position j. In Equation 8, p_1,j, p_2,j, p_3,j, etc. is the probability of codon i at positions 1, 2, 3, etc. In Equation 8, k is the total number of valid synonymous codons for the amino acid at position j. This formulation captures the degree of codon variability per position across the generated batch.

In some embodiments, a sequence-level diversity reward is computed by averaging positional entropy across the entire codon sequence. The total entropy reward is calculated as in Equation 9.

$$\text{entropy\_total} = (1/L) * (\text{H\_1} + \text{H\_2} + \ldots + \text{H\_L}) \quad \text{[Equation 9]}$$

In Equation 9, H_1, H_2, H_3, etc. Is the entropy at codon position 1, 2, 3, etc. In Equation 9, L is the total number of codon positions in the protein sequence. Higher entropy_total values reflect broader synonymous codon usage and are favored by the reward function. This encourages the model to explore multiple high-quality codon configurations rather than converging on a narrow or repeated set.

In another embodiment, codon-level diversity is assessed using the average pairwise Levenshtein distance among full-length codon sequences generated for the same protein. Let Lev (S_i, S_j) denote the Levenshtein distance between two codon sequences S_i and S_j. The inter-sequence diversity reward is then computed as in Equation 10.

$$\text{diversity\_lev} = 2/(n*(n-1)) \times (Lev(\text{S\_1, S\_2}) + Lev(\text{S\_1, S\_3}) + \ldots + Lev(\text{S\_}\{n-1\}\text{, S\_n})) \quad \text{[Equation 10]}$$

In Equation 10, n represents the number of codon sequences generated in the batch, and the summation includes all unique unordered sequence pairs (i, j) where i<j. Higher diversity_lev values reflect greater dissimilarity between generated sequences, thereby penalizing collapse to a single output form.

In certain embodiments, either entropy-based, Levenshtein-based, or a weighted combination of both diversity metrics may be employed in the reward function. The diversity component may be selectively activated or tuned based on application context, such as ensuring sufficient variability for library generation, avoiding immunogenic motifs, or adhering to host-specific codon constraints. The weight of the diversity term may be set manually or automatically adapted during training to balance diversity against other optimization goals.

Composite Reward and Configuration

In various embodiments of the present invention, the final scalar reward used during reinforcement learning is computed as a weighted sum of selected component scores, where each component represents a biologically relevant property, and each weight reflects its relative importance. The system is modularly designed to allow user-defined or application-specific configuration of the reward function. Each component may be activated, deactivated, or differently weighted depending on the desired biological outcome, production constraints, or regulatory goals.

In certain use cases, the composite reward function is tailored to different therapeutic or industrial applications by adjusting the relative weights of the underlying reward components. For instance, in mRNA vaccine design, the composite reward may emphasize high CAI to ensure robust expression in host cells, moderate deltaG to support transcript stability without excessive folding, and low GC penalty to avoid innate immune activation due to CpG motifs. In contrast, in recombinant protein expression systems, the reward may prioritize high CAI along with low repeat penalty to minimize translational stalling and moderate GC penalty to enhance process stability and cloning success. In gene therapy applications, components such as codon diversity and moderately negative deltaG may be assigned higher weights to improve transgene robustness, reduce immunogenicity, and enable more diverse synonymous sequence pools.

The weights associated with each reward component may be manually configured by the user, dynamically annealed during the course of training (e.g., increasing the weight of deltaG after early CAI convergence), or automatically optimized using techniques such as meta-learning or evolutionary tuning in future implementations. This configuration flexibility enables the reward function to be tailored to emerging use cases without requiring structural changes to the model architecture or training pipeline.

Reward Aggregation and Strategy

In various embodiments, the invention employs a reward aggregation strategy that combines multiple biologically informed metrics into a single scalar reward signal. This scalar reward is used to update the model parameters via reinforcement learning. Each metric corresponds to a distinct biological objective and is first normalized to a common numerical scale (e.g., [0,1]) to ensure comparability across heterogeneous criteria.

The general form of the aggregated reward function is given by Equation 11.

$$\text{total\_reward} = W1*R1 + W2*R2 + \ldots + Wn*Rn \quad \text{[Equation 11]}$$

In Equation 11, R1 through Rn represent the normalized scores for active reward components (such as codon adaptation index, GC content penalty, RNA folding energy, codon repeat penalty, and diversity metrics), and W1 through Wn are their respective scalar weights. The variable n denotes the number of reward components selected for inclusion in a given training configuration.

The reward weights W1 through Wn may be explicitly defined by the user, selected from predefined profiles tailored for common use cases, or determined automatically by the system. For instance, in some embodiments, a synthetic biology application expressing proteins in *E. coli* may prioritize high CAI and low GC content, whereas mRNA vaccine design may benefit from moderate CAI, favorable RNA folding energy (deltaG), and elevated codon diversity.

The invention supports multiple reward aggregation strategies that define how weights are applied and potentially adjusted during training. In one embodiment, a fixed-weight strategy is used, in which the weights are initialized at the start of training and remain constant. In another embodiment, a dynamic weighting strategy is applied, wherein weights are adjusted over time-such as linearly increasing the weight of the diversity term or annealing the CAI weight to prevent premature convergence. In yet another embodiment, adaptive reward tuning is employed using meta-learning algorithms or reinforcement-based meta-controllers, which iteratively optimize the reward weight configuration based on observed training performance or biological constraints.

To enhance training stability and ensure equitable metric contribution, each reward component may undergo post-processing. In some embodiments, each component score is clipped to a predefined range (e.g., [0.0, 1.0]) to reduce the influence of outlier values. Additionally, a running baseline, such as a moving average per reward component, may be subtracted or used for normalization to stabilize reward scaling over time. In certain configurations, the system may automatically rebalance the reward weights to mitigate dominance by a single component, especially in cases of class imbalance or conflicting optimization signals.

The set of reward components included in the aggregation may vary depending on the application. In minimal configurations, only a subset of the full reward space—such as CAI and deltaG—may be used. In more comprehensive embodiments, all five primary components (CAI, GC content, deltaG, codon repeat suppression, and diversity) may be employed simultaneously.

The final scalar reward produced by this aggregation process is used as the optimization signal in the reinforcement learning algorithm (e.g., REINFORCE). The modular structure and tunable flexibility of this reward aggregation scheme allow the invention to generalize across diverse biological systems, codon usage profiles, and therapeutic or industrial use cases.

Post Processing and Filtering

In various embodiments of the present invention, after codon sequences are generated and scored by the system, optional post-processing and filtering modules may be applied to further refine the output. These operations enable the enforcement of additional biological, regulatory, or synthesis-related constraints that are not directly optimized during the model's training phase. Post-processing steps may be applied in batch mode or per-sequence and are designed to improve suitability for real-world deployment.

In some embodiments, the post-processing module comprises one or more of the following operations, which may be independently enabled or configured. First, a restriction site screening module, wherein codon sequences are analyzed for the presence of undesired restriction enzyme recognition motifs (e.g., EcoRI, HindIII), and sequences containing such motifs are either removed or flagged to avoid disruption in downstream cloning or vector assembly. Second, a motif detection module, wherein generated sequences are scanned for biologically active or regulatory motifs such as polyadenylation signals, splice donor or acceptor sites, CpG islands, cryptic promoters, or immunogenic epitopes. Sequences matching one or more of these motifs may be excluded or annotated for user review. Third, a repeat and homopolymer detection module, wherein sequences containing long stretches of identical nucleotides or trinucleotide repeats (e.g., "AAAA," "GGGG") are filtered to reduce risks associated with synthesis failure, frameshifting, or translation slippage. Fourth, a codon usage conformity analysis module, wherein the codon distribution of each generated sequence is compared against a codon usage table for a specified host organism. Sequences that deviate beyond a configurable threshold may be penalized or removed. Fifth, a GC window smoothing module, wherein a sliding-window analysis (e.g., 30-nucleotide window) is applied to ensure that local GC content stays within a specified subrange, even when global GC content appears acceptable. This provides additional stability for synthesis and expression in challenging contexts.

In certain configurations, user-defined constraints may be imposed at inference time, overriding the weights or parameters used during model training. For example, a user may specify conditions such as: (a) enforce GC content between 48% and 52%, (b) exclude all sequences containing EcoRI sites, or (c) include only sequences with entropy above 0.60. These constraints may be defined through configuration files, API parameters, or interactive user interfaces.

In some embodiments, a post-processing ranking function is applied after filtering, wherein valid sequences are ranked based on a composite utility score that integrates both reward-based metrics and penalties from rule-based filters. Sequences that fail one or more filters may either be excluded or assigned lower ranks in the final output list.

The final set of filtered and ranked codon sequences may be exported in one or more output formats, including but not limited to FASTA, GenBank, CSV, or JSON. Each exported sequence may be accompanied by associated metadata, such as reward component scores, filtering annotations, unique sequence identifiers, host organism assumptions, and configuration profiles used during generation.

In some embodiments, post-processing rules are customizable through external configuration files, parameterized API calls, or graphical web interface toggles, allowing users to impose real-time biological or manufacturing constraints without requiring retraining or reparameterization of the underlying model.

These post-processing and filtering steps ensure that codon-optimized sequences generated by the system are biologically valid, synthetically feasible, and application-ready for use in downstream pipelines, including gene synthesis, therapeutic development, regulatory review, and high-throughput screening.

Actb Gene Optimization as a Worked Example

To demonstrate the performance and utility of the invention, one of the two representative protein targets selected for codon optimization was human beta-actin (ACTB). This example was chosen because of its distinct use case as a high-expression housekeeping genes. The ACTB gene encodes a highly conserved cytoskeletal protein and is frequently used in recombinant expression systems.

The native amino acid sequence was input to the codon generation system. Pptimized candidate sequences were then generated using an embodiment of the invention with a pretrained transformer model and RL-model.

A summarized tabulated comparison of the key metrics between natively occurring ACTB gene sequence and RL-optimized ACTB gene sequence is provided in Table 1.

Table 1: Comparison between biological metrics of naturally occurring sequence of ACTB gene and biological metrics of the mean of 100 sequences of ACTB gene generated using an embodiment of the claimed method

| Metric | Naturally occurring sequence of ACTB | Mean of RL-Optimized sequences of ACTB |
|---|---|---|
| CAI Score | 0.58 | 0.84 |
| GC Content Score | 61.6 | 60.3 |
| deltaG Score | 0.62 | 0.76 |
| Repeat Penalty | 0.957 | 0.95 |
| Entropy (positional) | 0.89 | 0.71 |

The resulting sequences were evaluated for each of the biological reward components, described in the following.

Figure 5:
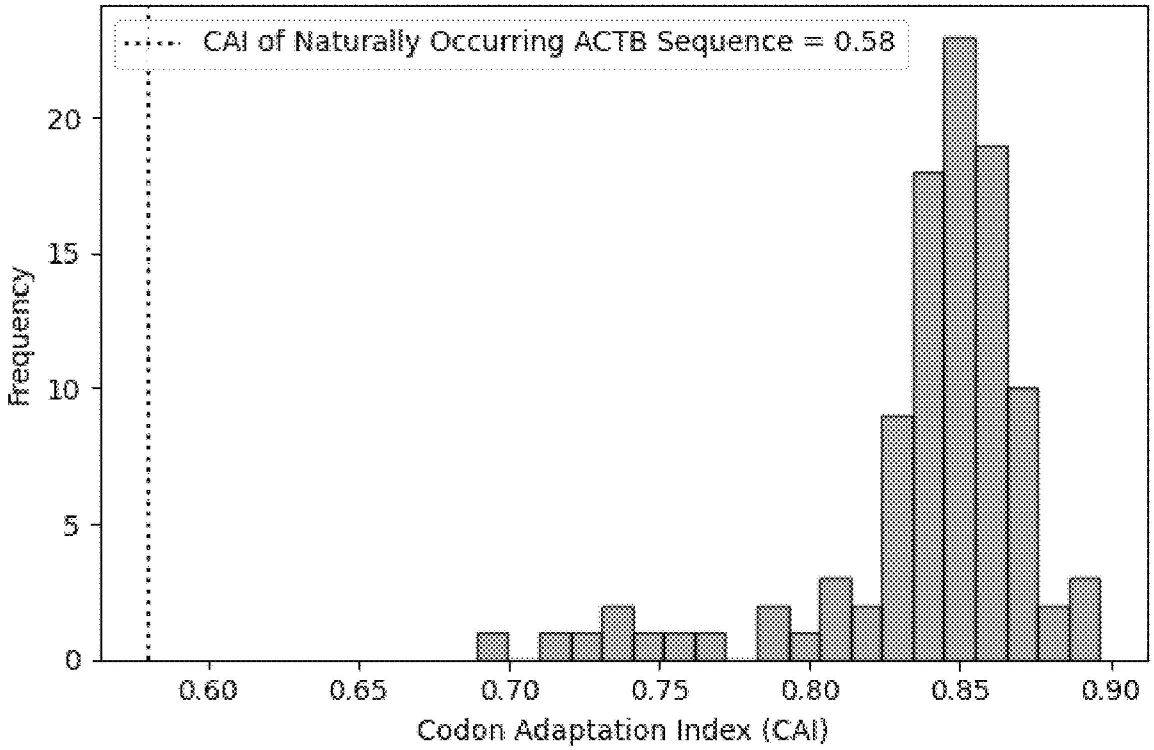
FIG. 5 is a histogram showing the distribution of codon adaptation index (CAI) values for 100 optimized sequences of an example ACTB gene, generated by an embodiment of the invention.

One of the reward components analyzed was CAI improvement. RL-optimized sequences exhibited a significant increase in CAI compared to the naturally occurring sequence of ACTB gene. The mean of this metric is compared in Table 1 with a naturally occurring ACTB gene sequence. A histogram of CAI distributions across 100 optimized samples of ACTB gene is shown in FIG. 5.

Figure 6:
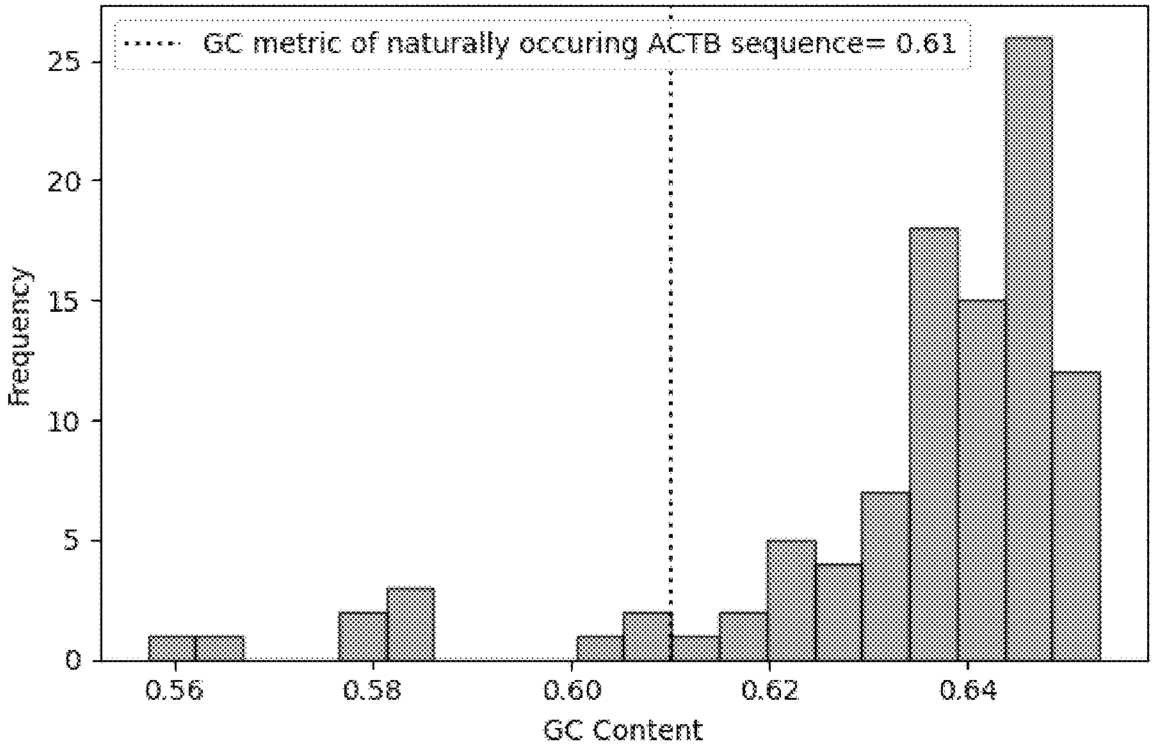
FIG. 6 is a histogram showing the distribution of GC content values for 100 optimized sequences of an example ACTB gene, generated by an embodiment of the invention.

One of the reward components analyzed was GC content stability. GC content was maintained near 50%, using Gaussian penalty shaping. The mean of this metric is also compared in Table 1 with a naturally occurring ACTB gene sequence. A histogram of GC content distributions across 100 optimized samples of ACTB gene is shown in FIG. 6.

Figure 7:
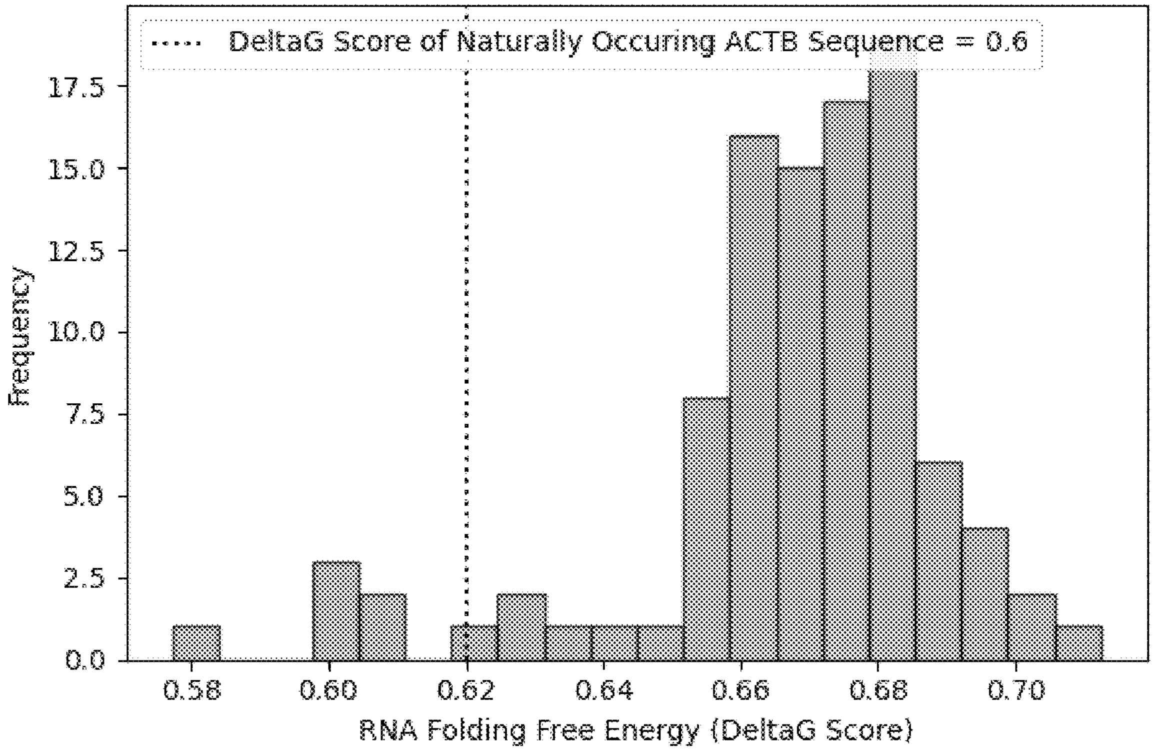
FIG. 7 is a histogram showing the distribution of RNA folding free energy (deltaG) scores for 100 optimized sequences of an example ACTB gene, generated by an embodiment of the invention.

One of the reward components analyzed was deltaG. RNAfold-based deltaG scores were higher (more stable) the RL-optimized sequences than in the naturally occurring sequences. The mean of this metric is also compared in Table 1 with a naturally occurring ACTB gene sequence. A histogram of deltaG score distributions across 100 optimized samples of ACTB gene is shown in FIG. 7.

Figure 8:
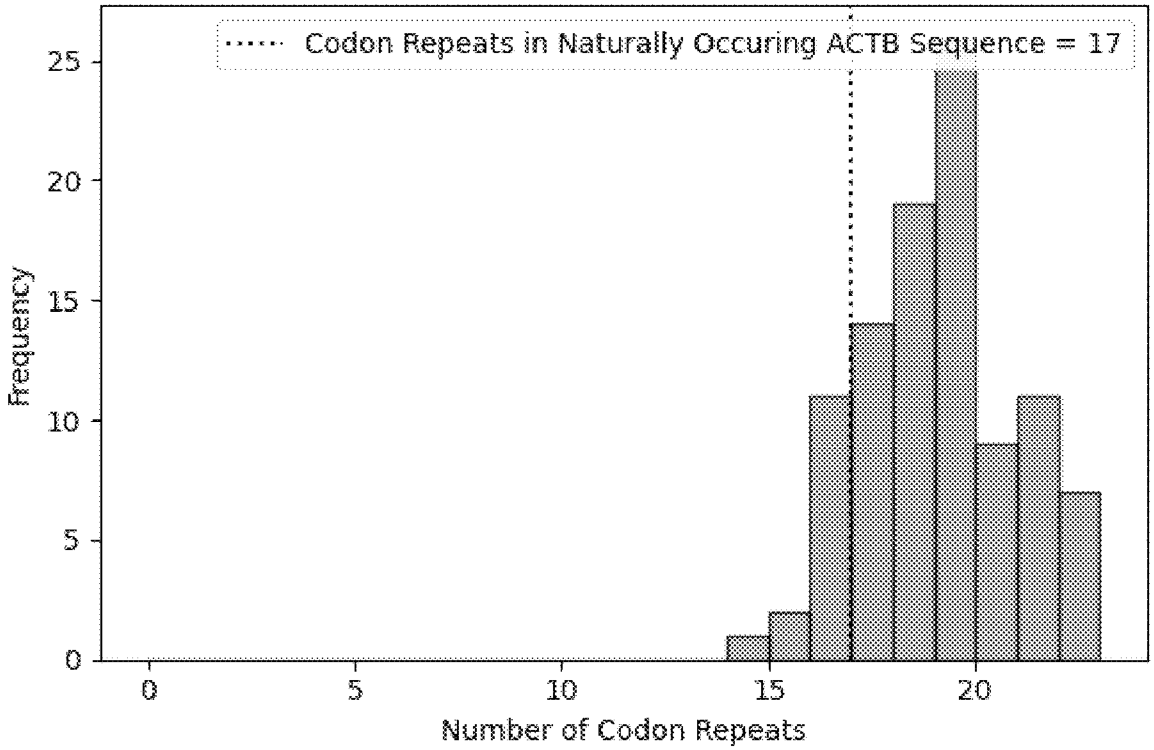
FIG. 8 is a histogram showing the distribution of consecutive mRNA codon repeats in 100 optimized sequences of an example ACTB gene, generated by an embodiment of the invention.

One of the reward components analyzed was repeat suppression. Codon repeat penalties were reduced, with repeat distributions. The mean of this metric is also compared in Table 1 with a naturally occurring ACTB gene sequence. A histogram of repeat penalty distributions across 100 optimized samples of ACTB gene is shown in FIG. 8.

Figure 9:
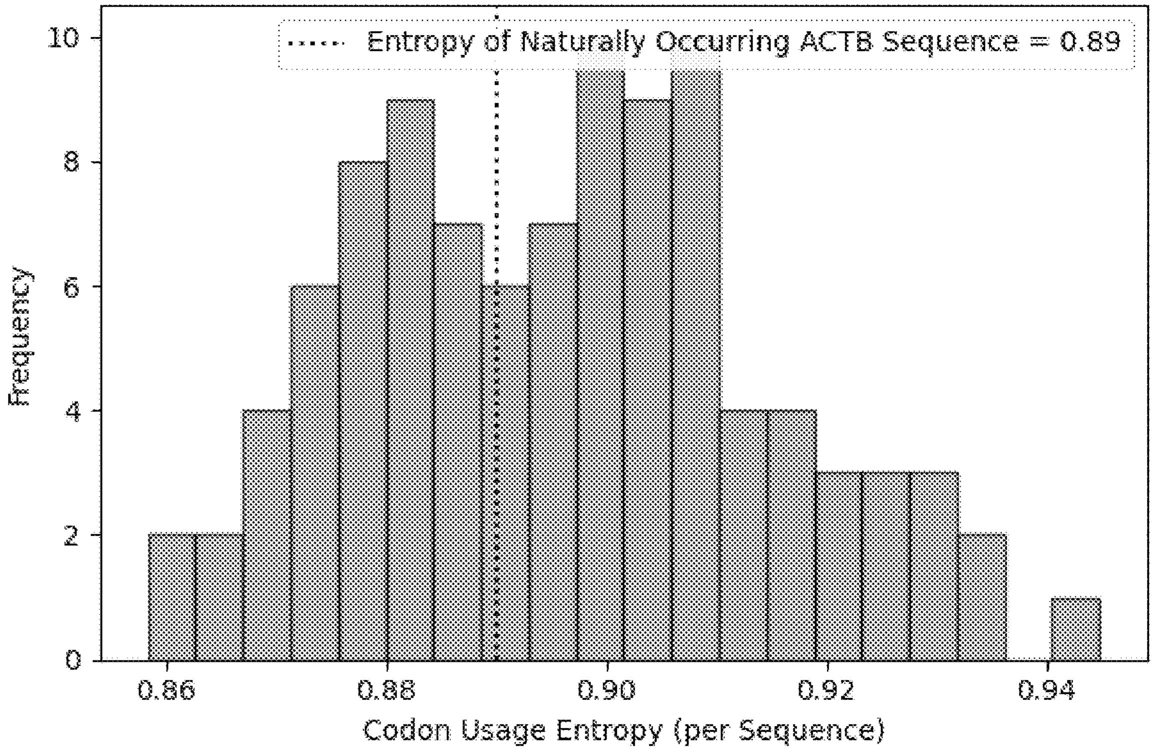
FIG. 9 is a histogram showing the distribution of positional entropy diversity in 100 optimized sequences of an example ACTB gene, generated by an embodiment of the invention.

One of the reward components analyzed was diversity, which was represented by entropy in this case. The average positional codon entropy showed a large diversity in spite of the optimization of multiple metrics. The mean of this metric is also compared in Table 1 with a naturally occurring ACTB gene sequence. A histogram of entropy distributions across 100 optimized samples of ACTB gene is shown in FIG. 9.

These results confirm the effectiveness of reinforcement learning for codon optimization across diverse biological goals. The model is not limited to maximizing CAI, but instead learns to balance trade-offs between multiple constraints, offering application-specific flexibility.

HLA-A Gene Optimization as a Worked Example

To demonstrate the performance and utility of the invention, one of the two representative protein targets selected for codon optimization was human leukocyte antigen A (HLA-A). The HLA-A gene was selected to evaluate codon optimization in a clinically relevant, polymorphic protein. Due to its high variability across alleles, it is important to generate diverse codon representations for this protein to support mRNA vaccine design, antigen presentation studies, or population-based screening.

A tabulated comparison of the key metrics between natively occurring HLA-A gene sequence and RL-optimized HLA-A gene sequence is provided in Table 2.

Table 2: Comparison between biological metrics of naturally occurring sequence of HLA-A gene and biological metrics of the mean of 100 sequences of HLA-A gene generated using an embodiment of the claimed method

| Metric | Naturally occurring sequence of HLA-A | Mean of RL-Optimized sequences of HLA-A |
|---|---|---|
| CAI Score | 0.53 | 0.79 |
| GC Content Score | 63.7 | 71.4 |
| deltaG Score | 0.71 | 0.78 |
| Repeat Count Penalty | 0.96 | 0.93 |
| Entropy (positional) | 0.91 | 0.92 |

These results demonstrate that the model can balance multiple objectives—including translational efficiency, diversity, and structural stability—within the same optimization framework.

These results confirm the effectiveness of reinforcement learning for codon optimization across diverse biological goals. The model is not limited to maximizing CAI, but instead learns to balance trade-offs between multiple constraints, offering application-specific flexibility.

Deployment and System Architecture

In various embodiments of the present invention, the system is implemented as a modular software architecture comprising components for input handling, codon sequence generation, reward computation, reinforcement learning, and output post-processing. The system may be deployed on local machines, cloud infrastructure, or within a containerized execution environment, and is compatible with CPU, GPU, or TPU acceleration.

In one embodiment, the system comprises a plurality of functionally distinct modules, each configured to execute a specific step within the codon optimization pipeline. An input handling module receives amino acid sequences and associated metadata, performs schema validation, and tokenizes the input for downstream processing. A codon generation module performs inference using a transformer-based or autoregressive language model to produce candidate synonymous codon sequences corresponding to the input protein. A synonym masking module may apply a codon-level logit mask during inference, constraining the model to output only valid synonymous codons for each amino acid position, thereby ensuring translational fidelity.

In some embodiments, a reward computation module evaluates each generated codon sequence using a composite scoring function comprising biological metrics such as codon adaptation index (CAI), GC content, RNA folding energy (deltaG), codon diversity, and repeat suppression. These metrics are normalized and aggregated to produce a scalar reward used during model training. A reinforcement learning module is configured to update model parameters using a policy gradient algorithm (e.g., REINFORCE), with the goal of maximizing the expected reward across generated sequences.

The system further comprises an output formatting module configured to compile optimized codon sequences and export them in user-specified formats, including but not limited to CSV, FASTA, or JSON. In some embodiments, a logging and checkpointing module maintains detailed training metadata such as reward progression, codon entropy, loss metrics, and system state. The logs may additionally include output-level statistics (e.g., mean CAI, average GC content, folding energy) as well as model-level metadata (e.g., architecture hash, configuration parameters, reward function version, codon usage tables). These logs support reproducibility, auditability, and version control of the codon optimization pipeline.

In certain embodiments, the system is deployed via a web API, allowing real-time interaction. Users may submit protein sequences and receive codon-optimized sequences via RESTful endpoints using JSON-formatted requests and responses. The API may include token-based or key-based authentication to ensure secure access. In other embodiments, the system is containerized using platforms such as Docker or Singularity, facilitating deployment on high-performance clusters, virtualized instances, or local environments without dependency conflicts.

The system supports parallelization of the reinforcement learning workflow using distributed training frameworks, including but not limited to PyTorch Distributed Data Parallel (DDP), Ray, or Horovod. This enables horizontal scaling across multiple compute nodes and accelerators, improving training efficiency for large-scale models.

In some embodiments, the system includes mechanisms for dynamic configuration and modular extensibility. For example, new protein sequences may be queued for inference via batch upload or API streaming, reward weightings may be modified through configuration files or user interfaces, and model checkpoints may be replaced or fine-tuned to incorporate organism-specific codon preferences. These features allow users to tailor system behavior to a wide range of biological contexts without modifying source code.

The system may be implemented using one or more open-source deep learning frameworks, including PyTorch, TensorFlow, or JAX. It may be distributed as a Python package, precompiled binary, container image, or virtual environment to ensure compatibility across operating systems and deployment targets.

In certain configurations, the system may expose a graphical user interface (GUI) that enables non-programmatic users, such as synthetic biologists or molecular biology core facility staff, to interact with the codon optimization pipeline using drag-and-drop workflows. This interface may provide visual feedback, export controls, parameter configuration panes, and batch processing capabilities.

Computer-Readable Medium Embodiment

In various embodiments, the present invention is embodied as a non-transitory computer-readable medium (CRM) comprising instructions that, when executed by one or more processors, cause the system to perform operations associated with codon optimization as described throughout this specification. This embodiment protects the software deployment, portability, and cross-platform use of the invention as a distributable product, executable across desktop, cloud, and edge environments.

The computer-readable medium may take the form of any non-transitory digital distribution format suitable for software delivery and execution. For example, the CRM may be embodied as an installable software archive (e.g., .whl, .tar.gz, .zip), a container image compatible with Docker or other OCI-compliant runtimes, or a compressed binary executable suitable for direct installation on a user device. In certain embodiments, the CRM is delivered as a firmware image for embedded processors, or as a software package pre-configured for hosted execution via a cloud platform. In some implementations, the software may be exposed via a programmatic interface, such as a RESTful web API, thereby enabling codon optimization as a remote service.

In some embodiments, the computer-readable instructions stored on the medium are configured to perform the following operations. The instructions accept a protein amino acid sequence as input, validate the format, and tokenize it for codon generation. The instructions invoke a transformer-based or autoregressive model to generate a corresponding nucleotide sequence consisting of synonymous codons. A synonym-masking operation is applied to constrain the model outputs to codons that preserve the original amino acid sequence. The instructions then compute a composite biological reward for the generated codon sequence, using one or more metrics selected from the group consisting of codon adaptation index (CAI), GC content, RNA folding energy (deltaG), codon diversity, and codon repeat penalties. If the system is operating in training mode, the instructions apply a reinforcement learning algorithm to update model parameters based on the computed reward. The optimized codon sequence, along with reward component metadata, is then exported in a structured format such as CSV, FASTA, or JSON.

In inference-only mode, the CRM includes a frozen model checkpoint, configuration files, and synonym masking tables. This enables deterministic codon generation without parameter updates. Reinforcement learning updates are disabled in this configuration, making it suitable for production deployment or regulated environments.

In training-enabled mode, the CRM further comprises reward shaping parameters, reinforcement learning engine components (e.g., REINFORCE loop), model optimizer settings, and logging infrastructure. Checkpointing and audit-trace modules are also included to support reproducibility and progressive learning.

In certain embodiments, the CRM may additionally include predefined input/output examples for verification, reference organism profiles for CAI and GC optimization, default or user-adjustable reward weight configurations, and optional graphical user interface (GUI) or command-line (CLI) tools for execution.

The invention may be executed in a variety of environments, including but not limited to standalone computing systems (e.g., laptops, workstations, servers), distributed computing clusters, virtualized environments, or embedded systems in automated synthesis platforms or laboratory robotics. Cloud-based execution is also supported via hosted container platforms or API gateways.

The CRM embodiment ensures that the invention may be protected not only as a method or system, but also as a software product delivered, distributed, or sold in executable form. This enables enforcement against unauthorized copying, redistribution, or unlicensed use of the codon optimization engine in commercial, research, or embedded contexts.

APPLICATIONS AND USE CASES

The invention described herein has broad applications in biotechnology, synthetic biology, therapeutics, and research. Its ability to generate biologically optimized codon sequences—customized across multiple biological constraints—makes it applicable in numerous protein-coding and mRNA-based workflows.

The system may be applied to a variety of domains in biotechnology, medicine, and synthetic biology. The system may be applied to mRNA vaccine design, wherein codon-optimized mRNA sequences with improved codon adaptation index (CAI), balanced GC content, and enhanced ΔG stability promote higher translation efficiency and molecular stability, both of which are critical for in vivo delivery. The system may be applied to gene therapy vector development, wherein codon tuning for viral delivery systems such as adeno-associated virus (AAV) or lentivirus improves gene expression while reducing immunogenic responses. The system may be applied to recombinant protein production, wherein codon optimization improves yield and reduces translational stalling in bacterial (e.g., *E. coli*) or mammalian (e.g., CHO, HEK293) expression systems. The system may be applied to synthetic biology workflows, wherein codon-level control enables design of orthogonal gene circuits, fine-tuning of metabolic pathways, and modulation of gene expression without altering the encoded protein sequence. The system may be applied to directed evolution and library design, wherein the diversity-aware codon generation process enables the synthesis of large, synonymous variant libraries that avoid codon bias and preserve functional diversity. The system may be applied to in vitro transcription systems, wherein codon sequences optimized for structural stability and GC content improve transcription efficiency and RNA folding in cell-free systems. The system may be applied to codon optimization as a service (COaaS), wherein the software platform is deployed as a commercial software-as-a-service (SaaS) or accessed via web API to support secure, on-demand codon sequence optimization. The system may be applied to educational or diagnostic applications, wherein it serves as a tool for teaching codon usage principles, simulating evolutionary conservation, or studying mutation tolerance in protein-coding regions.

The invention is adaptable to (a) different host organisms (e.g., *E. coli*, yeast, human, plant), (b) custom codon usage tables or non-standard genetic codes, or (c) multiple optimization goals (expression, diversity, regulation).

The configurability of the reward function, the modular system design, and the ability to plug in external codon usage tables or expression constraints make the invention well-suited for integration into bioinformatics pipelines, industrial-scale synthesis workflows, and gene design platforms.

This broad applicability ensures that the invention may be commercialized not only as a standalone tool but also embedded within larger bioengineering frameworks, licensed to pharmaceutical and biotech companies, or extended through future continuations to novel domains such as tRNA reprogramming, protein recoding, or synonymous immunogenicity minimization.

ADVANTAGES OVER PRIOR ART

The present invention provides several technical advantages over conventional codon optimization systems, including both rule-based academic tools and commercially available software. These advantages stem from the integration of data-driven codon generation, reinforcement learning, and biologically grounded multi-objective optimization, delivered through a modular, deployable architecture.

Unlike traditional methods that rely on static codon frequency tables or handcrafted scoring heuristics, the present invention employs a generative model that learns codon usage patterns from biological data and adapts to user-defined constraints through reinforcement learning. This enables the system to optimize not only for metrics such as codon adaptation index (CAI), but also for biologically meaningful tradeoffs across diverse applications, including vaccine design, gene therapy, and recombinant protein expression.

The invention includes multiple innovations that, when combined, represent a qualitative departure from prior art systems. These may be implemented independently or synergistically.

First, the invention introduces biologically shaped reward functions that apply smooth, differentiable transformations to key metrics. For example, CAI is shaped using a sigmoid function to avoid over-saturation at high values, while GC content is penalized using a Gaussian function centered at a desired target. This continuous shaping allows more stable training and biologically relevant optimization, in contrast to prior systems using hard cutoffs or linear score aggregation.

Second, the invention supports true multi-objective optimization by allowing composite rewards that combine CAI, GC content, RNA folding energy (deltaG), codon repetition penalties, and codon sequence diversity. Unlike legacy systems that focus exclusively on CAI, this invention enables customizable tradeoffs tailored to application-specific biological goals.

Third, the system incorporates a reinforcement learning framework, example such as using the REINFORCE algorithm, that updates the model policy using scalar feedback from the composite reward. This enables the model to optimize sequence generation in a direction that directly reflects functional biological outcomes, rather than relying on fixed scoring rules.

Fourth, the invention promotes synonymous codon diversity through entropy- and distance-based reward terms. These encourage the generation of multiple valid outputs per input protein, which is particularly beneficial for use cases such as immunogen design, directed evolution, and synthetic gene library generation.

Fifth, the system ensures translational fidelity through synonym-constrained inference. A codon mask is applied during decoding, restricting outputs to synonymous codons for each amino acid position. This guarantees that all generated sequences preserve the correct peptide sequence while allowing optimization within the bounds of the genetic code.

Sixth, the invention supports modular deployment. It can be implemented as a standalone executable, containerized service (e.g., Docker), web API, or command-line interface. This flexibility enables seamless integration into bioinformatics pipelines, cloud-based optimization platforms, and commercial software ecosystems. Moreover, it ensures enforceability across deployment modalities, including downloadable software and software-as-a-service.

Collectively, these advantages demonstrate that the present invention is not an incremental improvement but a fundamentally distinct approach to codon optimization. It combines learned generation, reward-driven tuning, and diversity-aware design to create an architecture that is not taught or suggested by any known combination of prior references. The invention thus offers a new paradigm for codon sequence design across research, therapeutic, and industrial applications.

The invention claimed is:

1. A computer-implemented method for generating an optimized codon sequence encoding a target polypeptide, the method executed by one or more processors coupled to a non-transitory computer-readable memory, the method comprising:

(a) receiving, by the one or more processors, an input amino-acid sequence defining the target polypeptide;

(b) generating, using an autoregressive transformer-neural-network-based codon-generation model stored in the memory, a candidate codon sequence corresponding to the input amino-acid sequence, wherein the autoregressive transformer-neural-network-based model comprises:

(i) an embedding layer configured to encode input tokens into vector representations, (ii) one or more transformer decoder layers configured to compute contextual representations from the vector representations, and (iii) an output layer configured to produce, at each codon position, a probability distribution over a codon vocabulary, wherein the autoregressive transformer-neural-network-based model generates each successive codon conditioned on the input amino-acid sequence and one or more previously generated codons, such that selection of a codon at position n is informed by codons generated at positions 1 through n−1;

(c) applying, by the one or more processors at each amino-acid position during generation of the candidate codon sequence, a synonym-mask constraint to the probability distribution produced by the output layer, the synonym-mask constraint setting to zero the probability of each codon that is not synonymous with the amino acid at that position according to a genetic code stored in the memory, thereby restricting codon selection at each position to valid synonymous codons;

(d) computing, by the one or more processors, a multi-objective biological-fitness reward for the candidate codon sequence, the reward comprising a weighted combination of at least two metrics selected from:

(i) codon adaptation index (CAI), (ii) guanine-cytosine (GC) content, (iii) predicted RNA folding free energy, (iv) codon repetition penalty, and (v) codon sequence diversity;

(e) updating, using a policy-gradient reinforcement-learning algorithm executed by the one or more processors, one or more parameters of the autoregressive transformer-neural-network-based model based on the computed multi-objective biological-fitness reward, wherein the policy-gradient reinforcement-learning algorithm computes a gradient of a log probability of the candidate codon sequence weighted by a difference between the reward and a baseline value, and wherein the updating modifies the probability distributions produced by the output layer to increase a likelihood of generating synonymous codons associated with higher reward values;

(f) iteratively performing steps (b) through (e) to generate a plurality of candidate codon sequences using successively updated parameters of the autoregressive transformer-neural-network-based model until a convergence criterion is satisfied;

(g) selecting, from the plurality of candidate codon sequences, an optimized codon sequence based on the computed multi-objective biological-fitness reward; and (h) outputting, by the one or more processors, the optimized codon sequence in a machine-readable nucleic-acid sequence format configured for integration with gene synthesis pipelines or bioinformatics tools.

2. A computer-implemented method for generating an optimized codon sequence encoding a target polypeptide for expression in a host organism, the method executed by one or more processors coupled to a non-transitory computer-readable memory, the method comprising:

(a) receiving an input amino-acid sequence defining the target polypeptide;

(b) generating, using an autoregressive transformer-neural-network-based codon-generation model stored in the memory, a candidate codon sequence corresponding to the input amino-acid sequence, wherein the autoregressive transformer-neural-network-based model generates each successive codon by:

(i) computing a probability distribution over a codon vocabulary conditioned on the input amino-acid sequence and all previously generated codons, and (ii) applying a synonym-mask constraint at the logit level prior to sampling, the synonym-mask constraint assigning zero probability to codons not synonymous with the amino acid at the current position;

(c) computing, by the one or more processors, a composite biological-fitness reward for the candidate codon sequence, the composite reward comprising:

(i) a codon adaptation index (CAI) component computed using a host-organism-specific codon usage table and shaped using a sigmoid function according to:

$$CAI\_score=1/(1+\exp(-k*(CAI\_raw-CAI\_target))$$

wherein CAI_raw is an unnormalized codon adaptation index, CAI_target is a configurable target threshold, and k is a steepness parameter;

(ii) a GC-content component shaped using a Gaussian penalty function according to:

$$GC\_penalty=\exp(-((GC\_actual-GC\_target)^{\wedge}2/(2*sigma^{\wedge}2)))$$

wherein GC_actual is an actual GC percentage of the candidate codon sequence, GC_target is a target GC percentage, and sigma is a configurable width parameter; and (iii) at least one additional component selected from: predicted RNA folding free energy normalized per nucleotide, a codon repetition penalty based on adjacent identical codons, and a codon sequence diversity score based on positional Shannon entropy;

(d) computing a total scalar reward as a weighted sum of the components in step (c), wherein weights are stored in the memory;

(e) updating parameters of the autoregressive transformer-neural-network-based model using a REINFORCE policy-gradient algorithm, wherein the REINFORCE algorithm computes a parameter update according to:

$$gradient=(reward-baseline)*gradient\ of\ \log P(candidate\ codon\ sequence)$$

wherein baseline is an exponential moving average of previous reward values;

(f) iteratively performing steps (b) through (e) until a convergence criterion is satisfied;

(g) selecting an optimized codon sequence from generated candidate codon sequences based on cumulative reward; and (h) outputting the optimized codon sequence in a format selected from FASTA, GenBank, CSV, or JSON, together with associated reward component values.

3. The method of claim 1, wherein the embedding layer encodes amino acid tokens and codon tokens into a shared embedding space, enabling joint learning across input and output domains.

4. The method of claim 1, wherein the one or more transformer decoder layers comprise self-attention mechanisms that compute contextual representations by attending to all previously generated codons.

5. The method of claim 1, wherein the autoregressive transformer-neural-network-based model further comprises positional encodings combined with the vector representations to encode sequential position information.

6. The method of claim 1, wherein the codon vocabulary comprises 64 canonical codons, and wherein the output layer produces logits over the 64 canonical codons prior to application of the synonym-mask constraint.

7. The method of claim 1, wherein the autoregressive transformer-neural-network-based model is replaced by an autoregressive long short-term memory (LSTM) network or a gated recurrent unit (GRU) network configured to generate codon sequences conditioned on the input amino-acid sequence and previously generated codons.

8. The method of claim 1, wherein the synonym-mask constraint is implemented using a precomputed lookup table stored in the memory, the lookup table indexed by amino acid and listing all valid synonymous codons for each amino acid according to a standard genetic code or a user-defined genetic code.

9. The method of claim 1, wherein the synonym-mask constraint is applied at a logit level by element-wise multiplication of the probability distribution with a binary mask vector, wherein each element corresponding to a non-synonymous codon is set to zero and each element corresponding to a synonymous codon is set to one.

10. The method of claim 1, wherein the synonym-mask constraint is applied during both training and inference of the autoregressive transformer-neural-network-based model, ensuring that all generated codon sequences preserve translational equivalence to the input amino-acid sequence.

11. The method of claim 1, wherein the codon adaptation index (CAI) is computed using a host-organism-specific codon usage table stored in the memory, wherein the host organism is selected from the group consisting of *Escherichia coli, Saccharomyces cerevisiae, Pichia pastoris*, CHO cells, HEK293 cells, and plant cells.

12. The method of claim 1, wherein the codon adaptation index (CAI) is shaped using a sigmoid function that produces a normalized score between 0 and 1, wherein higher scores indicate closer alignment with a configurable CAI target threshold.

13. The method of claim 1, wherein the GC-content metric comprises a Gaussian penalty function centered at a target GC percentage, wherein the Gaussian penalty function produces a score approaching 1 when the actual GC content equals the target and approaching 0 as deviation from the target increases.

14. The method of claim 1, wherein the GC content is computed globally over the entire candidate codon sequence, or locally within sliding windows of a predefined nucleotide length.

15. The method of claim 1, wherein the predicted RNA folding free energy is computed using a thermodynamic RNA secondary structure prediction tool and normalized on a per-nucleotide basis to account for sequence length, wherein a higher normalized score indicates a more favorable folding energy range.

16. The method of claim 1, wherein the codon repetition penalty is computed according to:

repeat_score=1−(repeat_count/(total_codons−1))

wherein repeat_count is a number of adjacent identical codons and total_codons is a total number of codons in the candidate codon sequence.

17. The method of claim 1, wherein the codon sequence diversity is computed using positional Shannon entropy calculated from an empirical distribution of codon usage across a batch of generated candidate codon sequences, wherein higher entropy indicates broader synonymous codon usage.

18. The method of claim 1, wherein the codon sequence diversity is computed using average pairwise Levenshtein distance among candidate codon sequences generated for the same input amino-acid sequence, wherein higher distance indicates greater dissimilarity between generated sequences.

19. The method of claim 1, wherein the baseline value is computed as an exponential moving average of previous reward values, and wherein subtracting the baseline from the reward reduces variance in the policy-gradient update.

20. The method of claim 1, wherein the reinforcement-learning algorithm further comprises an entropy regularization term added to a loss function to encourage exploration of diverse synonymous codon configurations and prevent early convergence to deterministic outputs.

21. A computer system for generating optimized codon sequences encoding target polypeptides, the system comprising:

(a) one or more processors;

(b) a non-transitory computer-readable memory operably coupled to the one or more processors and storing:

(i) an autoregressive transformer-neural-network-based codon-generation model comprising an embedding layer, one or more transformer decoder layers, and an output layer configured to produce probability distributions over a codon vocabulary, (ii) a synonym-mask constraint table indexed by amino acid, the table listing valid synonymous codons for each amino acid according to a genetic code, and (iii) one or more host-organism codon usage tables for computation of codon adaptation index;

(c) an input interface configured to receive an input amino-acid sequence defining a target polypeptide;

(d) a codon-generation module configured to execute on the one or more processors and to generate candidate codon sequences using the autoregressive transformer-neural-network-based model, wherein the codon-generation module applies the synonym-mask constraint at each amino-acid position to restrict codon selection to synonymous codons;

(e) a reward-computation module configured to execute on the one or more processors and to compute a multi-objective biological-fitness reward for each candidate codon sequence, the reward comprising a weighted combination of at least two metrics selected from codon adaptation index, GC content, predicted RNA folding free energy, codon repetition penalty, and codon sequence diversity;

(f) a reinforcement-learning module configured to update parameters of the autoregressive transformer-neural-network-based model using a policy-gradient algorithm based on the computed reward; and (g) an output interface configured to export an optimized codon sequence in a machine-readable nucleic-acid sequence format configured for integration with gene synthesis pipelines or bioinformatics tools.

22. The system of claim 21, wherein the memory further stores a plurality of host-organism codon usage tables, and wherein the system is configured to select a codon usage table based on a user-specified target host organism.

23. The system of claim 21, further comprising a graphical user interface configured to:

(i) receive user input specifying the input amino-acid sequence and optimization parameters, (ii) display reward component values and optimization progress during reinforcement learning, and (iii) present candidate codon sequences ranked by computed reward.

24. The system of claim 21, further comprising a web-based deployment module configured to expose an API endpoint that accepts amino-acid sequences via network requests and returns optimized codon sequences together with associated reward metadata.

25. The system of claim 21, wherein the one or more processors comprise a graphics processing unit (GPU) or tensor processing unit (TPU) configured to accelerate computations performed by the autoregressive transformer-neural-network-based model.

26. A non-transitory computer-readable storage medium storing instructions that, when executed by one or more processors, cause the one or more processors to:

(a) receive an input amino-acid sequence defining a target polypeptide;

(b) generate, using an autoregressive transformer-neural-network-based codon-generation model, a candidate codon sequence corresponding to the input amino-acid sequence, wherein the autoregressive transformer-neural-network-based model generates each successive codon conditioned on the input amino-acid sequence and previously generated codons;

(c) apply, at each amino-acid position during generation, a synonym-mask constraint that restricts codon selection to codons synonymous with the amino acid at that position by modifying a probability distribution produced by the model;

(d) compute a multi-objective biological-fitness reward for the candidate codon sequence, the reward comprising a weighted combination of at least two metrics selected from codon adaptation index, GC content, predicted RNA folding free energy, codon repetition penalty, and codon sequence diversity;

(e) update parameters of the autoregressive transformer-neural-network-based model using a policy-gradient reinforcement-learning algorithm based on the computed reward;

(f) iteratively generate candidate codon sequences using the updated model until a convergence criterion is satisfied;

(g) select an optimized codon sequence based on the computed reward; and (h) output the optimized codon sequence in a machine-readable format together with associated reward component values.

27. The non-transitory computer-readable storage medium of claim 26, wherein the instructions are configured to execute in an inference-only mode using a frozen model checkpoint and the synonym-mask constraint without updating model parameters.

28. The non-transitory computer-readable storage medium of claim 26, wherein the instructions are configured to execute in a training mode that performs the policy-gradient reinforcement-learning algorithm to update model parameters based on the computed reward.

29. The non-transitory computer-readable storage medium of claim 26, wherein the instructions further cause the one or more processors to store, for each candidate codon sequence, individual reward component scores and a total scalar reward value.

30. The non-transitory computer-readable storage medium of claim 26, wherein the machine-readable format is selected from the group consisting of FASTA, GenBank, CSV, and JSON.

* * * * *